US008993280B2

(12) United States Patent
Sato et al.

(10) Patent No.: US 8,993,280 B2
(45) Date of Patent: Mar. 31, 2015

(54) METHOD FOR PRODUCING ALKALOIDS

(75) Inventors: Fumihiko Sato, Kyoto (JP); Hiromichi Minami, Ishikawa (JP)

(73) Assignee: Kyoto University, Kyoto (JP)

( * ) Notice: Subject to any disclaimer, the term of this patent is extended or adjusted under 35 U.S.C. 154(b) by 830 days.

(21) Appl. No.: 12/664,142

(22) PCT Filed: Jun. 12, 2008

(86) PCT No.: PCT/JP2008/060759
§ 371 (c)(1),
(2), (4) Date: Mar. 5, 2010

(87) PCT Pub. No.: WO2008/153094
PCT Pub. Date: Dec. 18, 2008

(65) Prior Publication Data
US 2010/0184166 A1    Jul. 22, 2010

(30) Foreign Application Priority Data

Jun. 12, 2007  (JP) ................................ 2007-155069

(51) Int. Cl.
*C12P 17/12* (2006.01)
*C12N 15/70* (2006.01)
*C12N 15/81* (2006.01)
*C12N 15/82* (2006.01)

(52) U.S. Cl.
CPC ................ *C12P 17/12* (2013.01); *C12N 15/70* (2013.01); *C12N 15/81* (2013.01); *C12N 15/8243* (2013.01)
USPC ........................................................ 435/122

(58) Field of Classification Search
None
See application file for complete search history.

(56) References Cited

U.S. PATENT DOCUMENTS 6,506,378 B1 * 1/2003 Kang .......................... 424/93.21

FOREIGN PATENT DOCUMENTS

| JP | 11-178577 A | 7/1999 |
| JP | 11-178579 A | 7/1999 |
| JP | 2002-291487 A | 10/2002 |
| JP | 2004-121233 A | 4/2004 |
| JP | 2004-141019 A | 5/2004 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Allen et al., "RNAi-mediated Replacement of Morphine with the Nonnarcotic Alkaloid Reticuline in Opium Poppy", Nature Biotechnology, vol. 22, No. 12, Dec. 2004, pp. 1559-1566.

Choi et al., "Molecular Cloning and Characterization of Coclaurine N-Methyltransferase from Cultured Cells of *Coptis japonica*", J. Biological Chemistry, vol. 277, No. 1, Jan. 4, 2002, pp. 830-835.
Fujii et al., "Knockdown of Berberine Bridge Enzyme by RNAi Accumulates (S)-reticuline and Activates a Silent Pathway in Cultured California Poppy Cells", Transgenic Res, vol. 16, 2007, pp. 363-375.
Fumihiko Sato, Journal of Japan Foundation of Applied Enzymology, Feb. 1, 2008, vol. 42, pp. 79-80.
Ikezawa et al., "Molecular Cloning and Characterization of CYP719, A Methylenedioxy Bridge-Forming Enzyne That Belongs to a Novel P450 Family, from Cultured *Coptis japonica* Cells", J. Biolog. Chem., vol. 278, No. 40, Oct. 3, 2003, pp. 38557-38566.
Ikezawa et al., "Molecular Cloning and Characterization of CYP80G2, A Cytochrome P450 that Catalyzes an Intramolecular C-C Phenol Coupling of (S)-Reticuline in Magnoflorine Biosynthesis, from Cultured *Coptis japonica* Cells", J. Biological Chem., vol. 283, No. 14, Apr. 4, 2008, pp. 8810-8821.
Ito et al., "Transformation of Intact Yeast Cells Treated with Alkali Cations", J. Bacteriology, vol. 153, No. 1, Jan. 1983, pp. 163-168.
Minami et al., "Microbial Production of Plant Benzylisoquinoline Alkaloids", PNAS, vol. 105, No. 21, May 27, 2008, pp. 7393-7398.
Minami et al., Functional Analysis of Norcoclaurine Synthase in *Coptis japonica*, Journal of Biological Chemistry, vol. 282, No. 9, Mar. 2, 2007, pp. 6274-6282.
Morishige et al., "In Vivo Bioconversion of Tetrahydroisoquinoline by Recombinant Coclaurine N-Methyltransferase", Biosci. Biotechnol. Biochem, vol. 68, No. 4, 2004, pp. 939-941.
Morishige et al., "Molecular Characterization of the S-Adenosyl-L-Methonine: 3'-Hydroxy-N-methylcoclaurine 4'-O-Methyltransferase Involved in Isoquinoline Alkaloid Biosynthesis in *Coptis japonica*", J. of Biological Chem., vol. 275, No. 30 Jul. 28, 2000,pp. 23398-23405.
Oeda et al., "Expression of Rat Liver Cytochrome P-450MC cDNA in *Saccharomyces cerevisiae*", DNA, vol. 4, No. 3, 1985, pp. 203-210.
Park et al., "Antisense RNA-Mediated Suppression of Benzophenanthridine Alkaloid Biosysnthesis in Transgenic Cell Cultures of California Poppy", Plant Physiology, vol. 128 Feb. 2002, pp. 696-706.
Park et al., "Modulation of Berberine Bridge Enzyme Levels in Transgenic Root Cultures of California Poppy Alters the Accumulation of Benzophenanthridine Alkaloids", Plant Molecular Biology, vol. 51, 2003, pp. 153-164.
Rathbone et al., "Microbial Transformation of Alkaloids", Current Opinion in Microbiology, vol. 5, 2002, pp. 274-281.
Ro et al., "Production of the Antimalarial Drug Precursor Artemisinic Acid in Engineered Yeast", Nature, vol. 440, No. 13, Apr. 2006, pp. 940-943.
Roh et al., "Purification, Cloning, and Three-Dimensional Structure Prediction of *Micrococcus luteus* FAD-Containing Tyramine Oxidase", Biochemical and Biophysical Research Communications, vol. 268, 2000, pp. 293-297.

(Continued)

*Primary Examiner* — Richard Hutson
(74) *Attorney, Agent, or Firm* — Birch, Stewart, Kolasch & Birch, LLP

(57) ABSTRACT

The present invention provides a method for producing an alkaloid, for example, reticuline, comprising providing dopamine as a substrate for a series of actions of monoamine oxidase, norcoclaurine-6-O-methyltransferase, coclaurine-N-methyltransferase and 3'-hydroxy-N-methylcoclaurine-4'-O-methyltransferase.

15 Claims, 10 Drawing Sheets

(56) References Cited

OTHER PUBLICATIONS

Sakaki et al., "Organella-Targeted Expression of Rat Liver Cytochrome P450c27 in Yeast", J. of Biological Chemistry, vol. 267, No. 23, Aug. 15, 1992, pp. 16497-16502.

Schmidt et al., "Poppy Alkaloid Profiling by Electrospray Tandem Mass Spectrometry and Electrospray FT-ICR Mass Spectrometry after [ring-13C6]-tyramine Feeding", Phytochemistry vol. 68, 2007, pp. 189-202.

Zoller et al., "Oligonucleotide-Directed Mutagenesis Using M13-Derived Vectors: an Efficient and General Procedure for the Production of Point Mutations in any Fragment of DNA", Nucl. Acids Research, vol. 10, No. 20, 1982, pp. 6487-6500.

Extended European Search Report issued on Aug. 17, 2012 in the corresponding European Patent Application No. 08777168.9.

Hoover L K et al., "Biotransformation of dopamine to norlaudanosoline by *Aspergillus niger*", Biotechnology and Bioengineering, vol. 38, No. 9, Nov. 1991, pp. 1029-1033.

Inui Takayuki et al, "Overexpression of *Coptis japonica* norcoclaurine 6-0-methyltransferase overcomes the rate-limiting step in benzylsioquinoline alkaloid biosynthesis in cultured *Eschscholzia californica*", Plant and Cell Physiology, vol. 48, No. 2, Feb. 2007, pp. 252-262.

\* cited by examiner

Ptac: tac promoter
T7p: T7 promoter
T7t: T7 terminator

Fig.5

| Combination of genes | Reaction product |
|---|---|
| MAO + NCS<br>MAO + NCS + CNMT<br>MAO + NCS + 4'OMT<br>MAO + NCS + CNMT + 4'OMT | 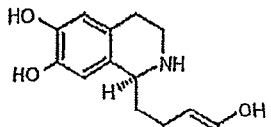<br>(S)-3'-hydroxynorcoclaurine<br>((S)-norlaudanosoline)) |
| MAO + NCS + 6OMT | 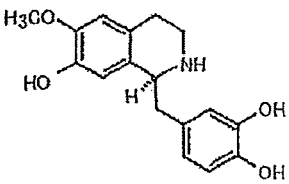<br>(S)-3'-hydroxycoclaurine |
| MAO + NCS + 6OMT + CNMT | 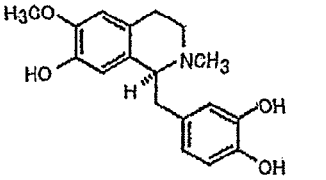<br>(S)-3'-hydroxy-N-methylcoclaurine |
| MAO + NCS + 6OMT + 4'OMT | 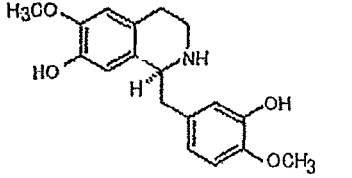<br>(S)-3'-hydroxy-4'-O-methylcoclaurine<br>(Norreticuline) |
| MAO + NCS + 6OMT + CNMT + 4'OMT | 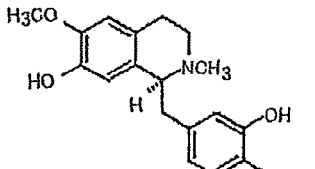<br>(S)-reticuline |

Fig.6-A

Fig.6-B a  Tyramine b  2-Phenylethylamine c  O-methyltyramine d  3-O-methyldopamine e  5-Hydroxydopamine f  Tryptamine

METHOD FOR PRODUCING ALKALOIDS

TECHNICAL FIELD

The present invention relates to a method for producing an alkaloid, particularly reticuline.

BACKGROUND ART

An isoquinoline alkaloid is a class of a variety of compounds ranging up to 6,000 kinds, and is an important useful secondary metabolite produced by plants, containing many useful pharmaceutical agents such as morphine and berberine. However, almost of their production relies on extraction from natural products.

Morphine and codeine which are an analgesic, and benzylisoquinoline alkaloids such as berberine, palmatine, and sanguinarine which are antibacterial agents are synthesized from tyrosine via (S)-reticuline in Magnoliaceae, Ranunculaceae, Berberidaceae, Papaveraceae, and other many plant species. (S)-reticuline is a branching point intermediate in biosynthesis pathways of many types of benzylisoquinoline alkaloids. That is, (S)-reticuline is a pharmaceutically important non-narcotic alkaloid which is useful in developing an anti-malaria agent and an anti-cancer agent. However, production of an alkaloid at a large scale using plants is difficult under the strict control of secondary metabolism in plants. In addition, chemical synthesis of an alkaloid is difficult because structures of alkaloids are complicated.

The present inventors isolated and identified many alkaloid biosynthesis genes from gene analysis of *Coptis* cells having high alkaloid biosynthesis activity. In addition, the present inventors have developed a method for producing a novel useful product, particularly reticuline which is an important intermediate metabolite by means of metabolic engineering using these genes (Patent Document 1).

In recent years, by application of plant metabolic engineering to a trial of increasing an amount of a final product of an alkaloid biosynthesis pathway, selected plant cells have become possible to produce a metabolite at an industrially applicable amount. With the development of metabolic engineering, development of novel useful drugs, using intermediates as substrates has been desired. However, only a few examples of successful cases in plant metabolic engineering as to accumulation of metabolic intermediates have been reported.

Production of reticuline has been reported in a transgenic opium poppy plant by means of RNAi of codeinone reductase (Non-Patent Document 1), and in a transgenic California poppy cell by means of RNAi of berberine bridging enzyme (BBE) (Non-Patent Document 2). The transgenic opium poppy is effective in producing reticuline, but there are problems that an amount of the product considerably varies for every plant or cultured cell, and that growth of a plant or a cultured cell needs a long time. Knockdown of the final step in morphine biosynthesis by means of RNAi of codeinone reductase induced accumulation of reticuline, but the mechanism of this accumulation could not be explained. In a study using an antisense method in order to suppress BBE in a California poppy cell and a root culture, accumulation of reticuline was not observed (Non-Patent Documents 3 and 4).

Like this, the production of reticuline which is an important intermediate, for example, in transformants has been tried. However, in systems using plant bodies or cultured cells, there are problems that a long time is necessary for proliferating it and that, in many cases, products exist as a mixture.

Recently, some trials of re-constituting entire biosynthesis steps in vitro have been investigated in microorganism systems (Non-Patent Documents 5 and 6). The microorganism system has excellent ability in improving not only an amount but also quality of a secondary metabolite since other plant metabolites are not inherently present in the microorganism system. The microorganism system gives some advantages to in vivo conversion of chemical substances, but there is drawback in it that availability of a substrate is limited, particularly, in a plant metabolism. A combination of a microorganism enzyme gene and a plant-derived gene is promising for establishing an effective and highly productive system of a variety of compounds.

Regarding benzylisoquinoline alkaloid pathway, almost all biosynthesis genes from norcoclaurine to berberine have been isolated, and their activities have been shown in microorganism systems (Non-Patent Documents 7 and 8). Since norcoclaurine synthase (hereinafter also referred to as NCS) catalyses coupling of dopamine and 4-hydroxyphenylacetaldehyde (hereinafter also referred to as 4-HPAA) in the benzylisoquinoline alkaloid pathway, it has been revealed that (S)-reticuline is produced via (S)-norcoclaurine. (S)-norcoclaurine is then converted into coclaurine by an action of norcoclaurine 6-O-methyltransferase (hereinafter also referred to as 6OMT), coclaurine is converted into N-methylcoclaurine by an action of coclaurine-N-methyltransferase (hereinafter also referred to as CNMT), N-methylcoclaurine is converted into 3'-hydroxy-N-methylcoclaurine (hereinafter also referred to as 6-O-methyllaudanosoline) by an action of P450 hydroxylase, and 3'-hydroxy-N-methylcoclaurine is converted into (S)-reticuline by an action of 3'-hydroxy-N-methylcoclaurine-4'-O-methyltransferase (hereinafter also referred to as 4'OMT) (see FIG. 1a).

[Patent Document 1] International Publication No. WO 2005/03305

[Non-Patent Document 1] Allen, R. S. et al. RNAi-mediated replacement of morphine with the nonnarcotic alkaloid reticuline in opium poppy. Nat. Biotechnol. 22, 1559-1566 (2004)

[Non-Patent Document 2] Fujii, N., Inui, T., Iwasa, K., Morishige, T.,& Sato, F. Knockdown of berberine bridge enzyme by RNAi accumulates (S)-reticuline and activates a silent pathway in cultured California poppy cells. Transgenic Research, 16:363-375 (2007)

[Non-Patent Document 3] Park, S. U., Yu, M., & Facchini, P. J. Antisense RNA-mediated suppression of benzophenanthridine alkaloid biosynthesis in transgenic cell cultures of California poppy. Plant Physiol. 128, 696-706 (2002)

[Non-Patent Document 4] Park, S. U., Yu, M., & Facchini, P. J.

Modulation of berberine bridge enzyme levels in transgenic root cultures of California poppy alters the accumulation of benzophenanthridine alkaloids. Plant Mol. Biol. 51, 153-164 (2003)

[Non-Patent Document 5] Rathbone, D. A., & Bruce, N. C. Microbial transformation of alkaloids. Curr. Opin. Microbial. 5, 274-281 (2002)

[Non-Patent Document 6] Ro. D. K. et al. Production of the antimalarial drug precursor artemisinic acid in engineered yeast. Nature 440, 940-943 (2006)

[Non-Patent Document 7] Minami, H. Dubouzet, E., Iwasa, K., & Sato, F. Functional analysis of norcoclaurine synthase in *Coptis japonica*. J. Biol. Chem. 282, 6274-6282 (2007)

[Non-Patent Document 8] Morishige, T., Tsujita, T., Yamada, Y., & Sato, F. Molecular characterization of the S-adenosyl-L-methionine: 3'-hydroxy-N-methylcoclaurine 4'-O-methyltransferase involved in isoquinoline alkaloid biosynthesis in *Coptis japonica*. J. Biol. Chem. 275, 23398-23405 (2000)

DISCLOSURE OF THE INVENTION

Problems to be Solved by the Invention

An object of the present invention is to establish a system for producing an alkaloid which is a useful intermediate for benzylisoquinoline alkaloids, particularly reticuline by a combination of microorganism and plant enzymes.

Means for Solving the Problems

The present inventors tried to perform re-construction of an alkaloid biosynthesis system using an enzymatic biological conversion method, or a heterogenous cell expression system by combining genes derived from a plant, for example, *Coptis* without using an isoquinoline alkaloid-producing plant cell. As a result, the present inventors found out a synthetic biological system which combines microorganism and plant enzymes for producing reticuline.

Reticuline which is an intermediate product of isoquinoline alkaloids is known to be biosynthesized via methylations at three stages and hydroxylation at one stage, after a condensation reaction of dopamine and 4-hydroxyphenylacetaldehyde (FIG. 1a). The present inventors found out that the step of hydroxylation can be omitted by using 3,4-dihydroxyphenylacetaldehyde (hereinafter also referred to as 3,4-DHPAA) in place of 4-hydroxyphenylacetaldehyde. Further, the present inventors found out that 3,4-dihydroxyphenylacetaldehyde can be synthesized from dopamine by using a microorganism (*Micrococcus luteus*)-derived monoamine oxidase (hereinafter also referred to as MAO). That is, the present inventors found out that effective reticuline synthesis only from dopamine becomes possible (FIG. 1b).

The present invention provides a method for producing an alkaloid which comprises using one or more amines including at least dopamine as a substrate, and providing the same for a series of actions of monoamine oxidase, norcoclaurine 6-O-methyltransferase, coclaurine-N-methyltransferase and 3'-hydroxy-N-methylcoclaurine-4'-O-methyltransferase. Preferably, the enzymatic reaction is performed in the presence of norcoclaurine synthase. Examples of amines other than dopamine used as a substrate include tyramine, 2-phenylethylamine, O-methyltyramine, 3-O-methyldopamine, 5-hydroxydopamine, tryptamine and the like. The present invention will be explained by referring to an example of the case where reticuline is produced using dopamine alone as a substrate.

The present invention provides a method for producing reticuline, which comprises providing dopamine as a substrate for a series of actions of MAO, 6OMT, CNMT and 4'OMT.

The method specifically comprises the steps of:
providing dopamine for an action of MAO to obtain 3,4-DHPAA,
reacting dopamine and 3,4-DHPAA to obtain 3'-hydroxynorcoclaurine,
providing 3'-hydroxynorcoclaurine for an action of 6OMT to obtain 3'-hydroxycoclaurine (hereinafter also referred to as norlaudanosoline),
providing 3'-hydroxycoclaurine for an action of CNMT to obtain 3'-hydroxy-N-methylcoclaurine, and
providing 3'-hydroxy-N-methylcoclaurine for an action of 4'OMT to obtain reticuline.

Herein, an origin of MAO is not particularly limited, but MAO is preferably derived from a microorganism, for example, *Micrococcus luteus, Escherichia coli, Arthrobacter aurescens*, or *Klebsiella aerogenes*.

Origins of 6 OMT, CNMT and 4'OMT are not particularly limited, but they are preferably derived from isoquinoline alkaloid-producing plants. Examples of the isoquinoline alkaloid-producing plants include isoquinoline alkaloid-producing plants such as Papaveraceae plants such as California poppy, opium poppy, corydalis tuber and the like, Berberidaceae plants such as *berberis* and the like, Rutaceae plants such as *amur cork* and the like, Magnoliaceae plants such as *kobus magnolia* and the like, Menispermaceae plants such as *Sinomenium acutum* and the like, as well as Ranunculaceae plants such as *Coptis* and the like, preferably, *Coptis*.

In the method of the present invention, the reaction of dopamine and 3,4-DHPAA may be performed by a chemical reaction without an enzymatic catalyst, or in the presence of NCS. The reaction is preferably performed in the presence of NCS. An origin of NCS is not particularly limited, but NCS is preferably derived from the isoquinoline alkaloid-producing plants as described above.

Specifically, in "in vivo reticuline production" explained below, when an *Escherichia coli* cell, an yeast cell, a *Bacillus subtilis* cell, a filamentous fungi cell, an insect cell, a mammal cell or the like is used as a host, the reaction of dopamine and 3,4-DHPAA may proceed by a chemical reaction even in the absence of NCS.

On the other hand, when an isoquinoline alkaloid non-producing plant cell is used as a host, NCS may be introduced for the reaction of dopamine and 3,4-DHPAA.

On the other hand, in "in vitro reticuline production" explained below similarly, the presence of NCS in addition to MAO, 6OMT, CNMT and 4'OMT is essential regardless of a cell used.

Like this, the reaction of dopamine and 3,4-DHPAA occurs by a chemical reaction in some cases, or by an action of NCS in some cases, depending on a production system used. For example, in a plant cell, dopamine is synthesized from L-DOPA with DOPA decarboxylase into a cytoplasm sol, is transported into a vacuole, and is compartmentalized into a vacuole. And, there is a possibility that this compartmentalization prevents chemical coupling of dopamine which is an amine, and 3,4-DHPAA which is an aldehyde. On the other hand, since dopamine is not compartmentalized in cells such as an *Escherichia coli* cell, it seems that chemical coupling of dopamine and 3,4-DHPAA is more prevalent than an enzymatic reaction of NCS.

The present invention also provides a method for producing reticuline from dopamine comprising the steps of:
providing a recombinant host cell expressing MAO, 6OMT, CNMT and 4'OMT, wherein the recombinant host cell is obtained by introducing genes encoding MAO, 6OMT, CNMT and 4'OMT into an isoquinoline alkaloid non-producing cell, and
culturing the recombinant host cell in the presence of dopamine.

In this method, since reticuline is produced in a recombinant host cell, such the method is referred to herein as "in vivo reticuline production".

In the method for producing reticuline in vivo, addition of dopamine as a substrate is essential, but addition of S-adenosylmethione (hereinafter also referred to as SAM) which is a methyl group donor in a methyltransferase reaction is not essential. That is, for example, when an *Escherichia coli* cell is used as a host, reticuline is produced in vivo without addition of SAM. In host cells such as an *Escherichia coli* cell, there is a system of reproducing SAM, and in vivo methylation activity seems to be maintained thereby.

A host cell used for the method for producing reticuline in vivo is an isoquinoline alkaloid non-producing cell and, when a host cell such as an *Escherichia coli* cell, an yeast cell, a *Bacillus subtilis* cell, a filamentous fungi cell, an insect cell, a mammal cell and the like is used, it is enough that genes encoding MAO, 6OMT, CNMT and 4'OMT are introduced.

However, also in the method for producing reticuline in vivo, it is preferable that a recombinant host cell expressing MAO, 6OMT, CNMT and 4'OMT further expresses a gene encoding NCS like an in vitro method explained below. A host cell in this case is not particularly limited as far as it is an isoquinoline alkaloid non-producing cell, and examples include an *Escherichia coli* cell, an yeast cell, a *Bacillus subtilis* cell, a filamentous fungi cell, an insect cell, a mammal cell, an isoquinoline alkaloid non-producing plant cell and the like.

The present invention further provides a method for producing reticuline from dopamine in vitro (hereinafter, also referred to as in vitro first method), which comprises the steps of:
providing a recombinant host cell expressing MAO, NCS, 6OMT, CNMT and 4'OMT, wherein the recombinant host cell is obtained by introducing genes encoding MAO, NCS, 6OMT, CNMT and 4'OMT into an isoquinoline alkaloid non-producing cell,
obtaining an enzyme extract containing MAO, NCS, 6OMT, CNMT and 4'OMT from the recombinant host cell,
providing a mixture of the enzyme extract and dopamine, and
producing reticuline from the mixture.

In addition, the present invention further provides a method for producing reticuline from dopamine in vitro (hereinafter, also referred to as in vitro second method), which comprises the steps of:
providing a group of cells expressing MAO, NCS, 6OMT, CNMT and 4'OMT, wherein the group of cells consists of two or more types of cells each expressing one or more enzymes selected from the group consisting of MAO, NCS, 6OMT, CNMT and 4'OMT, and contains at least one type of an isoquinoline alkaloid non-producing cell,
obtaining an enzyme extract containing MAO, NCS, 6OMT, CNMT and 4'OMT from the group of cells,
providing a mixture of the enzyme extract and dopamine, and
producing reticuline from the mixture.

In the in vitro second method, a group of cells consisting of two or more types of cells is used. Each cell constituting such the group of cells expresses one or more enzymes selected from the group consisting of MAO, NCS, 6OMT, CNMT and 4'OMT. The group of cells as a whole expresses all of MAO, NCS, 6OMT, CNMT and 4'OMT. In addition, among types of cells constituting the group of cells, at least one type is an isoquinoline alkaloid non-producing cell.

In the in vitro first and second methods, since reticuline is produced using an enzyme extract obtained from a cell or cells expressing MAO, NCS, 6OMT, CNMT and 4'OMT, these methods are referred as "in vitro reticuline production".

In the in vitro first method, an enzyme extract from one type of cell in which genes encoding MAO, NCS, 6OMT, CNMT and 4'OMT are introduced is used. In the in vitro second method, a combination of enzyme extracts from two or more types of cells is used. In any method, the enzyme extract essentially contains MAO, NCS, 6OMT, CNMT and 4'OMT. In addition, in any method, it is necessary to add dopamine as a substrate.

In the in vitro reticuline production, since SAM is contained in the enzyme extract, reticuline can be produced without adding SAM as a methyl donor. However, since SAM cannot be reproduced in vitro, when reticuline is produced in vitro at a large scale, it is preferable to add SAM to the mixture of the enzyme extract and dopamine from the outside.

It is preferable that the isoquinoline alkaloid non-producing cell used in the in vitro first method is an *Escherichia coli* cell, an yeast cell, a *Bacillus subtilis* cell, a filamentous fungi cell, an insect cell, a mammal cell or an isoquinoline alkaloid non-producing plant cell. In addition, in the in vitro second method, types of cells expressing each enzyme are not particularly limited, but among cells constituting the group of cells, at least one type of cell is an isoquinoline alkaloid non-producing cell like the first method.

According to the in vitro reticuline production, (S)-reticuline is obtained.

The present invention also provides a recombinant microorganism with genes encoding monoamine oxidase, norcoclaurine 6-O-methyltransferase, coclaurine-N-methyltransferase and 3'-hydroxy-N-methylcoclaurine-4'-O-methyltransferase introduced therein, which is used for the method of the present invention. In the recombinant microorganism, it is preferable that a gene encoding norcoclaurine synthase is further introduced.

Effect of the Invention

According to the present invention, by introducing biosynthesis enzyme genes necessary for reticuline synthesis into a host cell, and bio-converting a substrate directly utilizing enzymes prepared in a large amount, or by applying a substrate directly into a host cell expressing necessary genes, only a product of interest can be produced at a high efficiency.

According to the present invention, a basis by which reticuline being a material for producing a variety of useful compounds can be produced at a large amount is constructed. Further, development of a novel drug discovery resource by means of further metabolism conversion using reticuline becomes possible. The method of the present invention can be also applied to the case where dopamine and amines other than dopamine are used together as substrates.

BRIEF DESCRIPTION OF THE DRAWINGS

FIG. 6-B shows LC-MS analysis of scoulerine produced by mixed culture of microorganisms.

FIG. 7-1 shows structures of, and results of LC-MS analyses of alkaloids obtained by using a variety of amines together with dopamine as substrates.

FIG. 7-2 shows structures of, and results of LC-MS analyses of alkaloids obtained by using a variety of amines together with dopamine as substrates.

FIG. 7-3 shows structures of, and results of LC-MS analyses of alkaloids obtained by using a variety of amines together with dopamine as substrates.

BEST MODE FOR CARRYING OUT THE INVENTION

Figure 1:
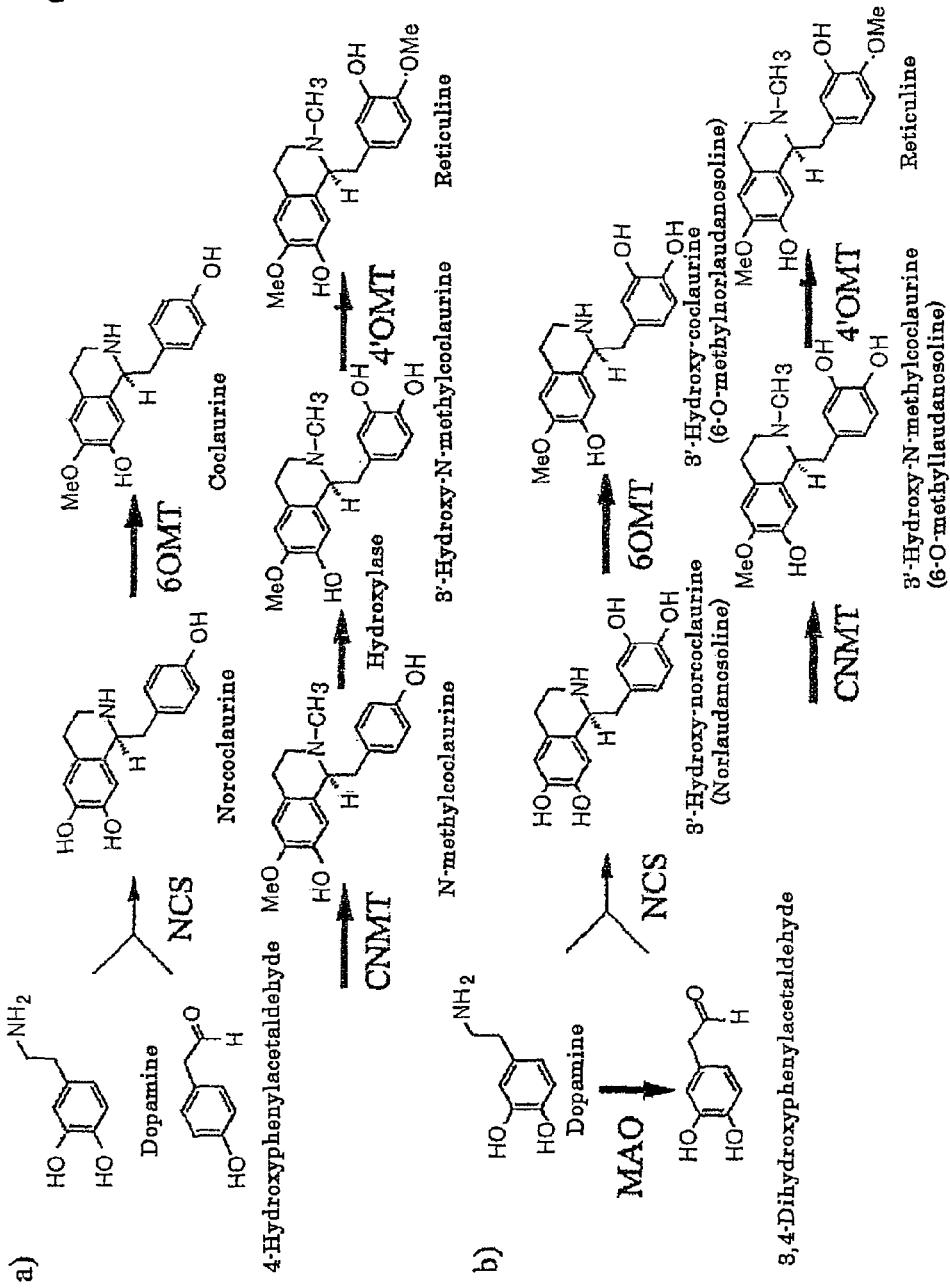
FIG. 1(*a*) shows a known reticuline synthesis pathway in plants, and FIG. 1(*b*) shows a reticuline synthesis pathway of the present invention.

Abbreviations 3,4-DHPAA: 3,4-Dihydroxyphenylacetaldehyde
4-HPAA: 4-Hydroxyphenylacetaldehyde
MAO: Monoamine oxidase
NCS: Norcoclaurine synthase
6OMT: Norcoclaurine 6-O-methyltrasferase
CNMT: Coclaurine-N-methyltransferase
4'OMT: 3'-Hydroxy-N-methylcoclaurine-4'-O-methyltransferase According to the method of the present invention, genes encoding enzymes involved in reticuline synthesis, monoamine oxidase (MAO), norcoclaurine synthase (NCS), norcoclaurine 6-O-methyltransferase (6OMT), coclaurine-N-methyltransferase (CNMT), and 3'-hydroxy-N-methylcoclaurine-4'-O-methyltransferase (4'OMT) are expressed in a host cell, enzymes are extracted from the host cell, the enzyme extracts are mixed in vitro, and reticuline is produced in the presence of dopamine which is a substrate, and S-adenosylmethionine which is a methylation donor. Alternatively, among them, genes encoding at least MAO, 6OMT, CNMT and 4'OMT are expressed in a host cell, and reticuline is produced in the cell by addition of dopamine.

Addition of SAM is not necessary in reticuline biosynthesis in host cells such as an *Escherichia coli* cell, an yeast cell, a *Bacillus subtilis* cell, a filamentous fungi cell, an insect cell, a mammal cell and the like, and addition of SAM is not essential also in reticuline synthesis by an enzyme extract since SAM contained in the enzyme extract can be utilized. When reticuline is synthesized at a large scale using the enzyme extract, it is preferable to add SAM.

The present invention provides a method for producing reticuline, which comprises providing dopamine which is a substrate, for a series of actions of MAO, 6OMT, CNMT and 4'OMT. Specifically, the method comprises the steps of:

providing dopamine for an action of MAO to obtain 3,4-DHPAA, reacting dopamine and 3,4-DHPAA to obtain 3'-hydroxynorcoclaurine.

providing 3'-hydroxynorcoclaurine for an action of 6OMT to obtain 3'-hydroxycoclaurine, providing 3'-hydroxycoclaurine for an action of CNMT to obtain 3'-hydroxy-N-methylcoclaurine, and providing 3'-hydroxy-N-methylcoclaurine for an action of 4'OMT to obtain reticuline.

In plant cells, it is known that reticuline is biosynthesized via methylation at three stages and hydroxylation at one stage, after a condensation reaction of dopamine and 4-hydroxyphenylacetaldehyde (4-HPAA), as shown in the synthesis pathway of FIG. 1a (FIG. 1a). On the other hand, in the present invention, the step of hydroxylation can be omitted by using 3,4-dihydroxyphenylacetaldehyde (3,4-DHPAA) instead of 4-hydroxyphenylacetalkehyde. Further, in the present invention, 3,4-dihydroxyphenylacetaldehyde can be synthesized from dopamine by using MAO. That is, according to the present invention, effective reticuline synthesis from only dopamine has become possible (FIG. 1b).

In the method of the present invention, a source from which dopamine is available is not particularly limited, but dopamine is obtained, for example, from Nakalai-Tesque (Kyoto, Japan), Wako Pure Chemical Industries, Ltd. (Osaka, Japan), or Sigma Aldrich (Missouri, St. Lewis, USA).

In addition, in the method of the present invention, four enzymes of MAO, 6OMT, CNMT and 4'OMT are necessary. Further, it is preferable to use NCS.

Examples of an origin of MAO include *Micrococcus luteus, Escherichia coli, Arthrobacter aurescens*, and *Klebsiella aerogenes*, and it is preferable to use MAO derived from *Micrococcus luteus*.

Origins of 6OMT, CNMT, 4'OMT and NCS are not particularly limited, but those derived from isoquinoline alkaloid-producing plants are preferable. Examples of isoquinoline alkaloid-producing plants include isoquinoline alkaloid-producing plants such as Papaveraceae plants such as California poppy, opium poppy, corydalis tuber and the like, Berberidaceae plants such as berberis and the like, Rutaceae plants such as amur cork and the like, Magnoliaceae plants such as *kobus magnolia* and the like, Menispermaceae plants such as *Sinomenium acutum* and the like, as well as Ranunculaceae plants such as *Coptis* and the like, preferably, *Coptis*.

MAO, 6OMT, CNMT, 4'OMT and NCS which can be utilized for the present invention will be explained below.

MAO used for the present invention is not particularly limited as far as it has enzyme activity of catalyzing a reaction of converting dopamine into 3,4-DHPAA, NCS is not particularly limited as far as it has enzyme activity of catalyzing a reaction of converting dopamine and 3,4-DHPAA into 3'-hydroxynorcoclaurine, 6OMT is not particularly limited as far as it has enzyme activity of catalyzing a reaction of converting 3'-hydroxynorcoclaurine into 3'-hydroxycoclaurine, CNMT is not particularly limited as far as it has enzyme activity of catalyzing a reaction of converting 3'-hydroxycoclaurine into 3'-hydroxy-N-methylcoclaurine, and 4'OMT is not particularly limited as far as it has enzyme activity of catalyzing a reaction of converting 3'-hydroxy-N-methylcoclaurine into reticuline. For example, MAO derived from *Micrococcus luteus*, which is encoded by a nucleotide sequence shown in SEQ ID NO: 1 as well as NCS, 6OMT, CNMT and 4'OMT, all derived from *Coptis*, which are encoded by nucleotide sequences shown in SEQ ID NOS: 2, 3, 4 and 5 can be suitably used. As NCS, any NCS having NCS activity of catalyzing a reaction of amine and aldehyde can be used. As NCS, a variety of sequences have been reported, but an enzyme named CjPR10 shown in SEQ ID NO: 2, and a homolog thereof, as well as an enzyme named CjNCS are suitably used.

The enzyme used for the present invention is not limited, but is preferably a protein of the following (a) or (b):

(a) a protein consisting of an amino acid sequence encoded by a nucleotide sequence of SEQ ID NO: 1, 2, 3, 4 or 5;

(b) a protein consisting of an amino acid sequence in which one or a few amino acids are deleted, substituted or added in the amino acid sequence encoded by a nucleotide sequence of SEQ ID NO: 1, 2, 3, 4 or 5, and having enzyme activity of MAO, NCS, 6OMT, CNMT or 4'OMT.

As the protein used for the present invention, a protein of the following (b') is also exemplified: (b') a protein consisting of an amino acid sequence having 70% or more homology to an amino acid sequence encoded by a nucleotide sequence of SEQ ID NO: 1, 2, 3, 4 or 5, and having enzyme activity of MAO, NCS, 6OMT, CNMT or 4'OMT.

The protein of (b) is a protein in which amino acid mutation (deletion, substitution, addition) occurs to such an extent that the function of the protein (a) of "having enzyme activity of MAO, NCS, 6OMT, CNMT, or 4'OMT" is not lost. Such the mutation also includes artificial mutation in addition to naturally occurring mutation. A means of generating artificial mutation is not limited to, but includes site-directed mutagenesis (Nucleic Acids Res. 10, 6487-6500, 1982). The number of mutated (deleted, substituted, added) amino acids is not particularly limited as far as the enzyme activity of the protein (a) is not lost, but is preferably 50 amino acids or less, more preferably 30 amino acids or less.

The protein of (b') is also a protein having homology with the protein of (a) to such an extent that the function of the protein (a) of "having enzyme activity of MAO, NCS, 6OMT, CNMT, or 4'OMT" is not lost. Homology is preferably 50% or more, and particularly preferably 70% or more.

In the present invention, "homology" means an extent of similarity of sequences between two polypeptides or polynucleotides, and is determined by comparing two sequences aliened in the optimal state (the state where matches of sequences become maximum) over a region of an amino acid sequence or a nucleotide sequence to be compared. The numerical value (%) of homology is calculated by determining the same amino acids or nucleotides present in both (amino acid or nucleotide) sequences, determining the number of matched sites, then, dividing the number of the matched sites with the total number of amino acids or nucleotides in a sequence region to be compared, and multiplying the resulting numerical value with 100. Examples of an algorism for obtaining optimal alignment and homology include various algorisms (e.g. BLAST algorism, FASTA algorism etc.) which are usually available to a person skilled in the art. Homology of amino acid sequences is determined using sequence analysis software such as BLASTP and FASTA. Homology of nucleotide sequences is determined using software such as BLASTN and FASTA.

Whether a protein has enzyme activity of MAO, NCS, 6OMT, CNMT, or 4'OMT or not can be determined by adding each reaction substrate to the protein preparation, and investigating whether a reaction product of each enzyme has been produced or not. The presence or the absence of activity can be determined by adding dopamine, and investigating whether 3,4-DHPAA has been produced or not regarding MAO, can be determined by adding dopamine and 3,4-DHPAA, and investigating whether 3'-hydroxynorcoclaurine has been produced or not regarding NCS, can be determined by adding 3'-hydroxynorcoclaurine, and investigating whether 3'-hydroxycoclaurine has been produced or not regarding 6OMT, can be determined by adding 3'-hydroxycoclaurine, and investigating whether 3'-hydroxy-N-methylcoclaurine has been produced or not regarding CNMT, and can be determined by adding 3'-hydroxy-N-methylcoclaurine, and investigating whether reticuline has been produced or not regarding 4'OMT.

Whether a product is 3,4-DHPAA, 3'-hydroxynorcoclaurine, 3'-hydroxycoclaurine, 3'-hydroxy-N-methylcoclaurine, or reticuline or not, can be confirmed by any means well-known to a person skilled in the art. Specifically, a product can be identified by providing the product, and each authentic product of 3,4-DHPAA, 3'-hydroxynorcoclaurine, 3'-hydroxycoclaurine, 3'-hydroxy-N-methylcoclaurine, or reticuline to LC-MS, and comparing the resulting spectra. Alternatively, a product can be also confirmed by comparing NMR analyses of the product and a corresponding authentic product.

Then, a gene encoding MAO, NCS, 6OMT, CNMT, or 4'OMT which can be used for the present invention will be explained.

Examples of the gene encoding MAO, NCS, 6OMT, CNMT, or 4'OMT, which is suitably used for the present invention include a gene having a nucleotide sequence shown in SEQ ID NO: 1, 2, 3, 4 or 5, respectively.

That is, the gene used for the present invention is not limited, but is preferably a gene which is a DNA of the following (a) or (b):
(a) a DNA consisting of a nucleotide sequence of SEQ ID NO: 1, 2, 3, 4 or 5;
(b) a DNA which hybridizes with a DNA consisting of a nucleotide sequence complementary to the DNA of the nucleotide sequence of (a) under the stringent condition, and encoding a protein having enzyme activity of MAO, NCS, 6OMT, CNMT, or 4'OMT.

Further, examples of the gene used for the present invention also include a gene which is a DNA of the following (c).
(c) a DNA consisting of a nucleotide sequence having 70% or more homology with the nucleotide sequence of SEQ ID NO: 1, 2, 3, 4 or 5, and encoding a protein having enzyme activity of MAO, NCS, 6OMT, CNMT, or 4'OMT.

Herein, the stringent condition refers to a condition under which only specific hybridization occurs, and non-specific hybridization does not occur. Such the condition is usually around 6M urea, 0.4% SDS, 0.5×SSC. A DNA obtained by hybridization has desirably 60% or higher homology, more preferably 80% or higher homology with the DNA consisting of the nucleotide sequence of (a).

Herein, the "homology" is as described above.

A method for confirming whether a protein encoded by a gene "has enzyme activity of MAO, NCS, 6OMT, CNMT, or 4'OMT" is as described above for a protein.

The gene can be obtained by PCR or hybridization technique well-known to a person skilled in the art, or may be artificially synthesized using a DNA synthesizer or the like. Determination of a sequence can be performed using a sequencer by a conventional method.

Then, the "in vivo reticuline production" will be explained.

The present invention provides a method for producing reticuline from dopamine, which comprises the steps of:
providing a recombinant host cell expressing MAO, 6OMT, CNMT, and 4'OMT, wherein the recombinant host cell is obtained by introducing genes encoding MAO, 6OMT, CNMT, and 4'OMT into an isoquinoline alkaloid non-producing cell, and
culturing the recombinant host cell under the presence of dopamine.

Preferably, the recombinant host cell further expresses a gene encoding NCS.

The host cell is not particularly limited as far as it is an isoquinoline alkaloid non-producing cell, but examples include an *Escherichia coli* cell, an yeast cell, a *Bacillus subtilis* cell, a filamentous fungi cell, an insect cell, a mammal cell and an isoquinoline alkaloid non-producing plant cell. Alternatively, when the host cell is selected from the group consisting of an *Escherichia coli* cell, an yeast cell, a *Bacillus subtilis* cell, a filamentous fungi cell, an insect cell, and a mammal cell, reticuline can be produced without introducing a gene encoding NCS into the host cell.

That is, when the host cell is selected from the group consisting of an *Escherichia coli* cell, an yeast cell, a *Bacillus subtilis* cell, a filamentous fungi cell, an insect cell, and a mammal cell, since compartmentalization of dopamine does not occur in cells, chemical coupling of dopamine and 3,4-DHPAA proceeds even under the absence of NCS.

In the in vivo reticuline production, MAO, NCS, 6OMT, CNMT, 4'OMT and genes encoding them are as explained above.

When a gene is introduced into a host cell, the gene may be directly introduced, but it is preferable that a vector with the gene introduced therein is introduced into the host. All of genes to be introduced may be contained in the same vector, or may be contained in two or more separate vectors.

As the vector with the gene introduced therein, a vector constructed for gene recombination from a plasmid or a phage which can be replicated autonomously in a host cell is suitable. It is preferable that the vector contains a replication origin suitable for a host cell in which the vector is introduced, a selectable marker, an expression control sequence such as a promoter and the like, and a terminator. Examples of the plasmid vector, for example, when expressed in *Escherichia coli*, include pET vectors, pQE vectors, and pGold vectors and, when expressed in yeast, include pYES2 vectors and pYEX vectors.

Examples of the selectable marker include an antibiotic-resistant gene such as an ampicillin-resistant gene and a streptomycin-resistant gene.

It is preferable that the expression vector contains an expression controlling sequence. The expression controlling sequence means a sequence which, when properly connected with a DNA sequence, can express the DNA sequence in a host cell. The expression controlling sequence contains at least a promoter. The promoter may be a constitutive promoter or an inducible promoter. Further, a transcription terminating signal, that is, a terminator region is preferably contained in the expression vector.

The expression vector used for the present invention can be made by adding suitable restriction enzyme recognizing sites to termini of the gene by a conventional method.

Examples of a method for transforming the expression vector into a host cell include any previously known methods, for example, a calcium chloride method, and an electroporation method.

Then, a recombinant host cell with genes encoding MAO, 6OMT, CNMT, and 4'OMT and, optionally, NCS introduced therein is cultured in the presence of dopamine.

It is preferable that dopamine is usually added so that a final concentration becomes 1 to 5 mM.

The culturing condition is not particularly limited as far as it is a condition under which a recombinant host cell is grown well, and each enzyme encoded by an introduced gene is sufficiently expressed, exhibiting each enzyme activity. Specifically, the culturing condition may be appropriately selected in view of a nutriophysiological nature of a host, and culturing is usually performed by liquid culturing. Examples of carbon sources of a medium include glucose and glycerol, and examples of nitrogen sources include ammonium sulfate, and casamino acid. In addition, salts, certain amino acids, certain vitamins and the like can be used, if desired.

A culturing temperature can be appropriately changed in such a range that a host cell is grown, and expresses an enzyme of interest, and the activity thereof is exhibited, for example, in the case of *Escherichia coli*, culturing condition of a temperature of 20° C., for 24 hours, and pH 7.0 can be used.

Expression of the enzyme of interest can be confirmed by an assay of the enzyme activity. That is, the expression can be confirmed by assaying conversion from a substrate of the objective enzyme into a product.

Production of reticuline can be confirmed by any means well-known to a person skilled to the art. Specifically, the production can be identified by providing the reaction product and a reticuline authentic product to LC-MS, and comparing the resulting spectra. Alternatively, the production can be also confirmed by comparison by NMR analyses between the reaction product and the reticuline authentic product.

In addition, in the in vivo reticuline production, addition of SAM is not particularly necessary since, in host cells such as an *Escherichia coli* cell, there is a reproduction system of SAM, thereby, in vivo methylation activity seems to be maintained.

Examples of methods for recovering reticuline include a method which comprises recovering a medium in which a host cell is suspended, passing the medium through a solid phase extraction cartridge (Sep-pak etc.) to adsorb alkaloid thereon, and eluting reticuline with MeOH to recover it.

Then, the "in vitro reticuline production" will be explained. In the specification and claims, the "in vitro" means cell-free system.

In addition, in the in vitro reticuline production, explanation for MAO, NCS, 6OMT, CNMT, 4'OMT and genes encoding them is as described above for the "in vivo reticuline production".

First, the in vitro first method is a method for producing reticuline from dopamine in vitro, which comprises the steps of:

providing a recombinant host cell expressing MAO, NCS, 6OMT, CNMT, and 4'OMT, wherein the recombinant host cell is obtained by introducing genes encoding MAO, NCS, 6OMT, CNMT, and 4'OMT into an isoquinoline alkaloid non-producing cell, obtaining an enzyme extract containing MAO, NCS, 6OMT, CNMT, and 4'OMT from the recombinant host cell, providing a mixture of the enzyme extract and dopamine, and producing reticuline from the mixture.

In the in vitro first method, the host cell is one type of a cell expressing all of MAO, NCS, 6OMT, CNMT, and 4'OMT.

A method for obtaining the enzyme extract containing MAO, NCS, 6OMT, CNMT, and 4'OMT from such the recombinant host cell is not particularly limited as far as the resulting extract contains active MAO, NCS, 6OMT, CNMT, 4'OMT and SAM. For example, the host cell is recovered by centrifugation, cells are ground, and the supernatant of cells obtained by centrifugation can be used as the enzyme extract.

On the other hand, the in vitro second method is a method for producing reticuline from dopamine in vitro, which comprises the steps of:

providing a group of cells expressing MAO, NCS, 6OMT, CNMT, and 4'OMT, wherein the group of cells consists of two or more types of cells each expressing one or more enzymes selected from the group consisting of MAO, NCS, 6OMT, CNMT, and 4'OMT, and contains at least one type of an isoquinoline alkaloid non-producing cell, obtaining an enzyme extract containing MAO, NCS, 6OMT, CNMT, and 4'OMT from the group of cells, providing a mixture of the enzyme extract and dopamine, and producing reticuline from the mixture.

The group of cells used for the in vitro second method consists of two or more types of cells expressing one or more enzymes selected from the group consisting of MAO, NCS, 6OMT, CNMT, and 4'OMT. The group of cells, as a whole, expresses all of MAO, NCS, 6OMT, CNMT, and 4'OMT. At least one type of cells constituting the group of cells is an isoquinoline alkaloid non-producing cell.

The group of cells refers to a population of two or more types of cells. Each of cells constituting the group of cells expresses one or more enzymes selected from the group consisting of MAO, NCS, 6OMT, CNMT, and 4'OMT, and may be cells derived from the same organism, or may be cells derived from different organisms.

A method for obtaining an enzyme extract containing MAO, NCS, 6OMT, CNMT, and 4'OMT from the group of cells is not particularly limited as far as the resulting extract contains active MAO, NCS, 6OMT, CNMT, 4'OMT and SAM. For example, a group of cells is recovered by centrifugation, then the group of cells is combined, and ground, and the supernatant of the group of cells obtained by centrifugation may be used as an enzyme extract, or each of cells constituting the group of cells are separately recovered by centrifugation, cells are ground, and supernatants of each of cells obtained by centrifugation may be combined, and used as an enzyme extract.

It is preferable that the enzyme extract contains a conventionally used buffer (Good buffer) such as Tris, HEPES, MOPS buffers and the like, and it is preferable that a pH is adjusted to 6 to 8.

The step of producing reticuline using the mixture of the enzyme extract and dopamine is the same as in the first and second methods. The condition of this step is not particularly limited as far as it is a condition under which respective enzymes of MAO, NCS, 6OMT, CNMT, and 4'OMT exhibit sufficiently enzyme activities. The mixture of the enzyme extract and dopamine essentially contains active MAO, NCS, 6OMT, CNMT, and 4'OMT as well as SAM, and contains dopamine added as a substrate. An addition amount of dopamine is usually a final concentration of 1 to 5 mM.

Examples of conditions of the step of producing reticuline using the mixture of the enzyme extract and dopamine include a condition of 37° C. and a pH of 7.5.

In the in vitro first method and the second method, it is preferable that the isoquinoline alkaloid non-producing cell is a cell selected from the group consisting of an *Escherichia coli* cell, an yeast cell, a *Bacillus subtilis* cell, a filamentous fungi cell, an insect cell, a mammal cell, and an isoquinoline alkaloid non-producing plant cell.

In the in vitro first method and the second method, since the mixture of the enzyme extract and dopamine contains SAM derived from a cell from which the enzyme has been extracted, it is not necessary to further add SAM. However, in order to obtain reticuline at a large amount, it is preferable to add SAM since, in the enzyme extract, a re-production system of SAM inherent to a cell does not work.

In the in vitro first method and the second method, a method for confirming production of the resulting reticuline is the same as that of the method in vivo, and examples of a method for recovering the resulting reticuline include a method which comprises precipitating a protein from the enzyme extract by a well-known method, passing it through a solid phase extraction cartridge (Sep-pak etc.) to adsorb alkaloid thereon, and eluting reticuline with MeOH to recover it.

According to the method for producing reticuline in vitro of the present invention, optically active (S)-reticuline is obtained. An optical purity can be measured by optical isomer separation with HPLC using a chiral column or specific rotation measurement using a polarimeter.

While the method for producing reticuline using dopamine as a substrate has been explained above, the method of the present invention can be also used for producing alkaloids other than reticuline using co-presence of dopamine and other amines. Examples of amines other than dopamine used as a substrate include tyramine, 2-phenylethylamine, O-methyltyramine, 3-O-methyldopamine, 5-hydroxydopamine, and tryptamine. When such the amines are used, in addition to reticuline, norcoclaurine, N-methylcoclaurine, 4'-O-methyl-N-methylcoclaurine (all above, in the co-presence of tyramine), 7-isoquinolinol, 1,2,3,4-tetrahydro-6-methoxy-1-(phenylmethyl)-, 7-isoquinolinol, 1,2,3,4-tetrahydro-6-methoxy-2-methyl-(phenylmethyl)- (all above, in the co-presence of 2-phenylethylamine), 4'-O-methylnorcoclaurine, 4'-O-methyl-N-methylnorcoclaurine, 4'-O-methyl-N-methylcoclaurine (all above, in the co-presence of O-methyltyramine), 3'-O-methylnorcoclaurine, 3'-O-methyl-N-methylcoclaurne, 3'-O-methylreticuline (all above, in the co-presence of 3-O-methyldopamine), 3',5'-dihydroxynorcoclaurine, 3',5'-dihydroxy-4'-O-methylcoclaurine (all above, in the co-presence of 5-hydroxydopamine), or 6-O-methyl-7-hydroxy-indolylmethyl-1,2,3,4-tetrahydroisoquinoline (in the co-presence of tryptamine) is produced, respectively.

EXAMPLES

Summary of Examples

In order to produce a benzylisoquinoline alkaloid in *Escherichia coli*, the present inventors modified a benzylisoquinoline alkaloid pathway (FIG. 1b). Benzylisoquinoline alkaloid biosynthesis begins at conversion of tyrosine into dopamine and 4-HPAA, and dopamine and 4-HPAA are condensed by NCS to produce (S)-norcoclaurine. However, since these initial steps have not been well-characterized yet, reconstruction of the production system for producing a variety of benzylisoquinoline alkaloids effectively is difficult.

In order to simplify such the complicated situation, monoamine oxidase (MAO), NCS, 6OMT, CNMT and 4'OMT were used for synthesizing reticuline. By means of coupling dopamine and 3,4-dihydroxyphenylacetamide (3,4-DHPAA), a step of hydroxylase by CYP80B could be omitted. Since MAO does not seem to have a role in alkaloid biosynthesis in opium poppy (Schmidt, J., Boettcher, C., Kuhnt, C., Kutchan, T. M., & Zenk, M. H. Poppy alkaloid profiling by electrospray tandem mass spectrometry and electrospray FT-ICR mass spectrometry after [ring-$^{13}C_6$]-tyramine feeding. Phytochemistry 68, 189-202 (2007)), MAO derived from a microorganism was introduced into a reticuline biosynthesis system, and 3,4-DHPAA was synthesized by deamination of dopamine by MAO.

When an expression vector containing all enzymes was constructed as a single vector, and this was expressed in *Escherichia coli*, reticuline could be produced from dopamine in both of in vivo (in an *Escherichia coli* cell) and in vitro (an enzyme extraction from *Escherichia coli*) systems.

For reticuline production in a microorganism system, reticuline biosynthesis genes were expressed in transgenic *Escherichia coli*. By adding 2 mM dopamine to a medium, the transgenic *Escherichia coli* produced (R,S)-reticuline into the medium at a yield of 1.7 mg/L culture medium within 20 hours. In biosynthesis of reticuline by a recombinant *Escherichia coli* cell, (R,S)-reticuline was obtained at a yield of 11 mg/L by increasing a concentration of dopamine to be added up to 5 mM.

(R,S)-reticuline was produced without adding S-adenosyl-L-methionine (SAM) which is a methyl-group donor. As reported previously, this was thought that a reproduction system of SAM in an *Escherichia coli* cell is useful for maintaining in vivo methylation activity during bioconversion (Morishige, T., Choi, K. B., & Sato, F. In vivo bioconversion of tetrahydroisoquinoline by recombinant coclaurine N-methyltransferase. Biosci. Biotechnol. Biochem. 68, 939-941 (2004)).

NCS stereospecifically produced an optical isomer, (S)-form, while reticuline produced in an *Escherichia coli* cell was in a racemic form. Also in an *Escherichia coli* cell expressing four reticuline biosynthesis genes (MAO, 6OMT, CNMT and 4'OMT) other than NCS, (R,S)-reticuline in a racemic form was produced at the same level (data not shown). These results show that although NCS is produced in an active form (data not shown), it could not function well in an *Escherichia coli* cell. This result shows that a condensation reaction of forming norcoclaurine occurred as a chemical reaction.

In order to investigate high production of reticuline in vitro, an enzyme extract from the transgenic *Escherichia coli* cell was mixed with S-adenosylmethionine (SAM), thereby, reticuline could be synthesized. Surprisingly, (S)-reticuline was stereospecifically synthesized from dopamine and SAM with the enzyme extract without purification and fine adjustment of each enzyme level. In plant metabolic engineering by means of RNAi of codeinone reductase, (R)-form could not be excluded (Allen, R. S. et al. RNAi-mediated replacement of morphine with the nonnarcotic alkaloid reticuline in opium poppy. Nat. Biotechnol. 22, 1559-1566 (2004)), while the formation of (R)-reticuline was not detected in the system of the present inventors. (S)-reticuline was synthesized from 2 mM dopamine at a yield of 22 mg/L within 60 minutes.

Since the yield was sufficiently high, and there was no intermediate other than reticuline, it was easy to purify (S)-reticuline which is a reaction product, in the system of the present inventors. By increasing an addition amount of dopamine, 55 mg/L of (S)-reticuline was obtained using the enzyme extract expressed from the *Escherichia coli*. At 5 mM dopamine, the yield was low without addition of SAM, while at 2 mM dopamine, the synthesis rate was around 90% even in the case of addition of no SAM as compared with addition of SAM.

Methyltransferase enzymes measurably worked without addition of SAM (data not shown). The microorganism system of the present inventors can supply an optically active compound (S)-reticuline stably and in a shorter time, as compared with a fermentation system of plant cultured cells.

Example 1

Reticuline Synthesis in *Escherichia coli*

Reticuline which is an intermediate product of isoquinoline alkaloids is known to be biosynthesized via methylation at three stages and hydroxylation at one stage, after a condensation reaction of dopamine and 4-hydroxyphenylacetaldehyde (FIG. 1*a*). The present inventors found out that the step of hydroxylation can be omitted by using 3,4-dihydroxyphenylacetaldehyde in place of 4-hydroxyphenylacetaldehyde. Further, by using monoamine oxidase (MAO) derived from a microorganism (*Micrococcus luteus*), 3,4-dihydroxyphenylacetaldehyde can be synthesized from dopamine. That is, according to the present invention, effective reticuline synthesis from only dopamine becomes possible (FIG. 1*b*).

Experimental Procedure

Reagents

Dopamine was purchased from Sigma-Aldrich.
Construction of Expression Vectors pKK2232-3 and pACYC184 Containing Reticuline Biosynthesis Genes Tac promoter or T7 promoter was added upstream of each of genes encoding enzymes necessary for reticuline synthesis, MAO, norcoclaurine synthase (NCS (CjPR10, encoded by SEQ ID NO: 2)), norcoclaurine methyltranferase (6OMT), coclaurine-N-methyltransferase (CNMT), and 3'-hydroxy-N-methylcoclaurine-4'-O-methyltransferase (4'OMT), and the genes were incorporated into two types of expression vectors (FIG. 2). *Escherichia coli* BL21 (DE3) was transformed with these plasmids to construct an expression strain. Details are shown below.
1) Construction of expression vector pKK223-3 containing reticuline biosynthesis genes (MAO, NCS) (FIG. 2 left) Construction of expression vector pKK223-3 containing *Micrococcus luteus* MAO gene A full length *M. luteus* MAO cDNA was PCR-amplified to construct an *Escherichia coli* expression vector for MAO in pKK223-3. For PCR, the following oligonucleotides were used:

Forward primer, 5'TT<u>GAATTC</u>ATGAGCAACCCGCATGTCGTG3' (SEQ ID NO: 6) (this contained EcoRI restriction site before ATG initiation codon (underlined));

Reverse primer, 5'CT<u>AAGCTT</u>CAGGCGCGGATGTCCCGGAG3' (SEQ ID NO: 7) (this is complementary to 3' terminus of cDNA, and contained HindIII restriction site after TGA stop codon (underlined)).

PCR was performed under the following condition: a first denaturation step, 2 minutes, 94° C.; 30 cycles: a cycle consisting of denaturation at 94° C. for 15 seconds, annealing at 50° C. for 30 seconds, and DNA elongation at 68° C. for 90 seconds, and final elongation at 68° C. for 5 minutes (for this, KOD-plus DNA polymerase (TOYOBO CO., LTD.) was used). The PCR fragment was subcloned into pKK223-3 vector (Pharmacia) cut with EcoRI and HindIII restriction enzymes. *M. luteus* MAO cDNA fragment was placed under the control of TAC polymerase promoter in pKK223-3. Both strands of DNA insert were sequenced, and it was confirmed that no mutation was introduced during PCR amplification.
Construction of Expression Vector pKK223-3 Containing *Micrococcus luteus* MAO Gene and *Coptis* NCS Gene PCR was performed using, as a template of DNA, an expression vector pET41a containing *Coptis* NCS gene (Minami, H. et al. Journal of Biological Chemistry, 282-6274-6282 (2007)). For PCR, the following oligonucleotides were used:
Oligonucleotides for NCS Forward primer, 5'-AC<u>TCGCGA</u>TCCCGCGAAATTAATACG-3' (SEQ ID NO: 8) (this contained NruI restriction site before T7 polymerase promoter (underlined));

Reverse primer, 5'-CA<u>GGATCC</u>AGCAAAAAACCCCTCAAGAC-3' (SEQ ID NO: 9) (this is complementary to 3' terminus of cDNA, and contained BamHI restriction site after T7 terminator (underlined)).

Figure 2:
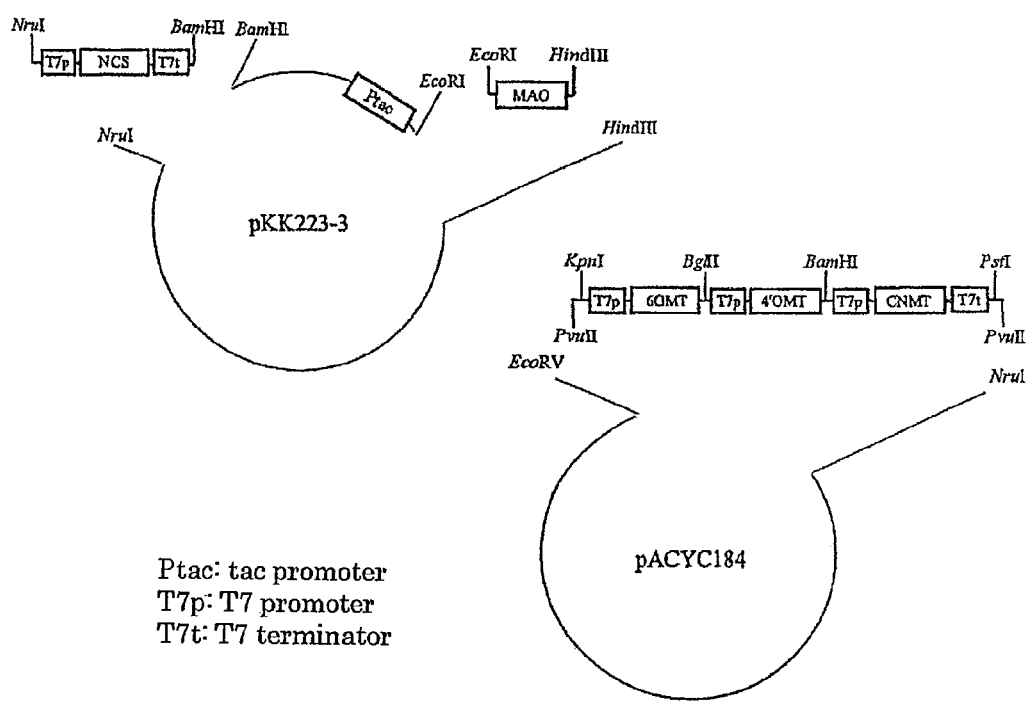
FIG. 2 shows a construct containing genes involved in reticuline synthesis.

The PCR fragment was subcloned into the expression vector pKK223-3 containing *M. luteus* MAO gene cut with NruI and BamHI restriction enzymes.
2) Construction of Expression Vector pACYC184 Containing Reticuline Biosynthesis Genes (6OMT, CNMT, 4'OMT) (FIG. 2 Right)

Construction of an *Escherichia coli* expression vector containing full length *Coptis* 6OMT, CNMT, and 4'OMT cDNAs was performed in the same manner as in the construction of the expression vector pKK223-3 containing *M. luteus* MAO gene. PCR was performed using, as a template of DNA, an expression vector pET21d containing *Coptis* 6OMT, CNMT, and 4'OMT genes (Morishige, T. et al. Journal of Biological Chemistry, 275, 23398-23405 (2000), Choi, K. B. et al. Journal of Biological Chemistry, 277, 830-835 (2002)). For PCR, the following oligonucleotides were used:

Oligonucleotides for 6OMT
    Forward primer, 5'A GGTACCGATCCCGCGAAATTAATACG3' (SEQ ID NO: 10) (this contained KpnI restriction site before T7 polymerase promoter (underlined));
    Reverse primer, 5'C AGATCTAATATGGATAAGCCTCAATCAC3' (SEQ ID NO: 11) (this is complementary to 3' terminus of cDNA, and contained BglII restriction site including TAG stop codon (underlined)).
Oligonucleotides for 4'OMT
    Forward primer, 5'C AGATCTGATCCCGCGAAATTAATACG3' (SEQ ID NO: 12) (this contained BglII restriction site before T7 polymerase promoter (underlined));
    Reverse primer, 5'T GGATCCTATGGAAAAACCTCAATGACTG3' (SEQ ID NO: 13) (this is complementary to 3' terminus of cDNA, and contained BamHI restriction site including TAG stop codon (underlined)).
Oligonucleotides for CNMT
    Forward primer, 5'T GGATCCGATCCCGCGAAATTAATACG3' (SEQ ID NO: 14) (this contained BamHI restriction site before T7 polymerase promoter (underlined));
    Reverse primer, 5'AC CTGCAGGCACGAAAAAACCCCTCAAGAC3' (SEQ ID NO: 15) (this is complementary to 3' terminus of cDNA, and contained PstI restriction site after T7 terminator (underlined)).

PCR fragments of three genes were subcloned into a pUC18 vector cut with KpnI and PstI restriction enzymes. From the expression vector pUC18 containing three genes, the PvuII-PvuII fragment was subcloned into pACYC184 vector cut with EcoRV and NruI restriction enzymes.

Expression of Recombinant Reticuline Biosynthesis Genes in *Escherichia coli*

Reticuline biosynthesis gene expression plasmids (pKK223-3 and pACYC184) were introduced into *Escherichia coli* DL21 (DE3). These recombinant *Escherichia coli* cells were cultured in 100 mL of LB medium containing 100 µg/ml of ampicillin and 50 µg/ml of chloramphenicol at 37° C. and 80 rpm. IPTG (isopropyl-β-D-thiogalactoside) was added to a final concentration of 1 mM at the time point at which $OD_{600}$ of *Escherichia coli* culture became 0.5. Cells were further cultured at 20° C. for 24 hours.

Cells were recovered by centrifugation at 8,000 rpm and 4° C. for 5 minutes. Pellets were re-suspended in 3 ml of extraction buffer (50 mM Tris-HCl (pH 7.5), 10% glycerol, 5 mM 2-mercaptoethanol), and ultrasound-treated with Sonic (Vibra-cell VC-130, Sonics & Materials Inc.) (60 seconds×three times at output set 15). The crude extract was centrifuged at 10,000×g for 5 minutes to obtain cell-free supernatant. The supernatant was used as an enzyme extract for in vitro reticuline synthesis.

Example 2

In Vivo Reticuline Biosynthesis

Reticuline biosynthesis in *Escherichia coli* cells was performed according to the same manner as that of the expression experiment of recombinant reticuline biosynthesis genes in *Escherichia coli* described above except for the following points.

Figure 3:
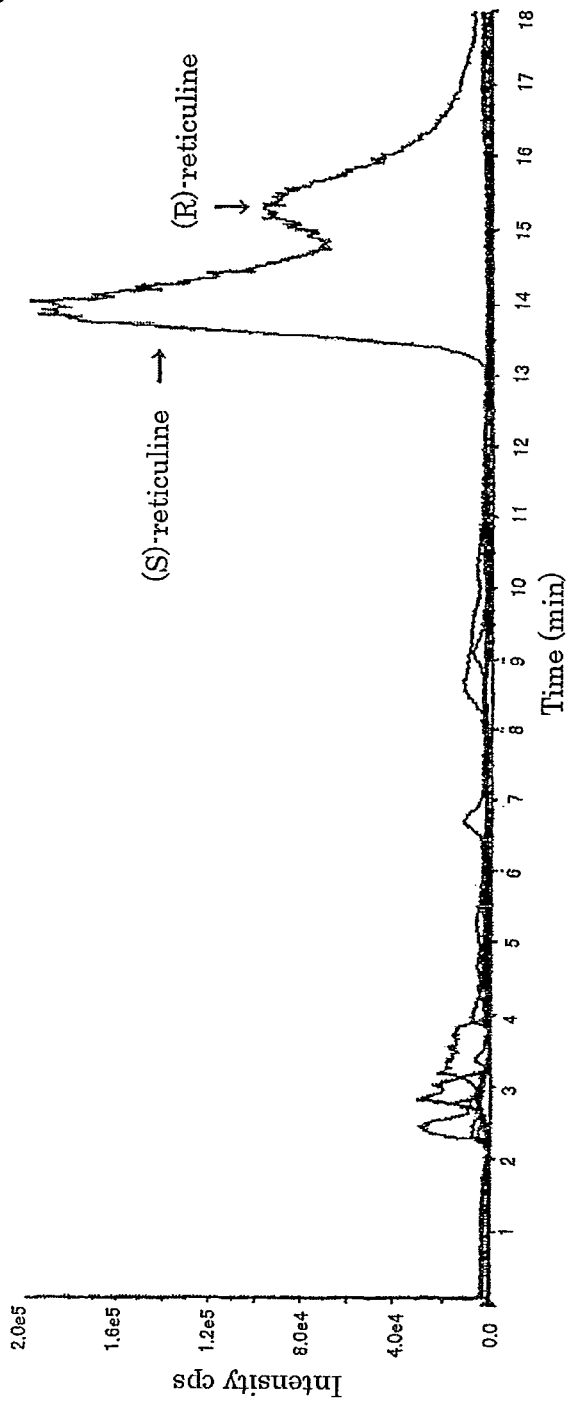
FIG. 3 shows LC-MS analysis of reticuline production in *Escherichia coli*.

At IPTG addition, dopamine was added to a final concentration of 2 mM. Cells were further cultured at 25° C. for 20 hours. The culture medium was centrifuged at 10,000×g for 5 minutes to remove bacterial cells. An equivalent amount of methanol was added to the centrifugation supernatant to remove proteins in the medium. Reticuline in the medium was measured by LC-MS (API 3200™ with Agilent™ HPLC system, Applied Biosystems Japan Ltd.).
Results
In Vivo Reticuline Biosynthesis Reticuline in the medium was measured and, as a result, (R,S)-reticuline was biosynthesized by the reticuline biosynthesis gene expression strain (FIG. 3). The yield was 1.7 mg/L. By increasing a concentration of dopamine to be added up to 5 mM, the yield of (R,S)-reticuline was increased up to 11 mg/L.

Example 3

In Vitro Reticuline Synthesis

In vitro reticuline synthesis was performed, and reticuline was measured by LC-MS. 100 µl of a standard enzyme reaction mixture consisted of the following: 100 mM Tris buffer, pH 7.5, 1 mM SAM (S-adenosylmethionine), 70 µl of the enzyme extract and 2 mM dopamine.

The reaction mixture was incubated at 37° C. for 60 minutes. The reaction was stopped by addition of an equivalent amount of methanol. After precipitation of proteins, the reaction product was measured qualitatively and quantitatively using LC-MS.

Reticuline Measurement by LC-MS

A sample was injected into ODS-80 Ts (Tosoh), and was eluted at a column temperature of 40° C. and a flow rate of 0.7 ml/min. The mobile phase was 40% acetonitrile+0.1% acetic acid. MS was ESI, and all products from dopamine to reticuline (m/z=153, 154, 288, 302, 316, 330) were measured at a positive mode. Quantification of reticuline was performed by measuring a peak area at m/z=330. A peak area was converted into a reticuline amount using a calibration curve.

Figure 4:
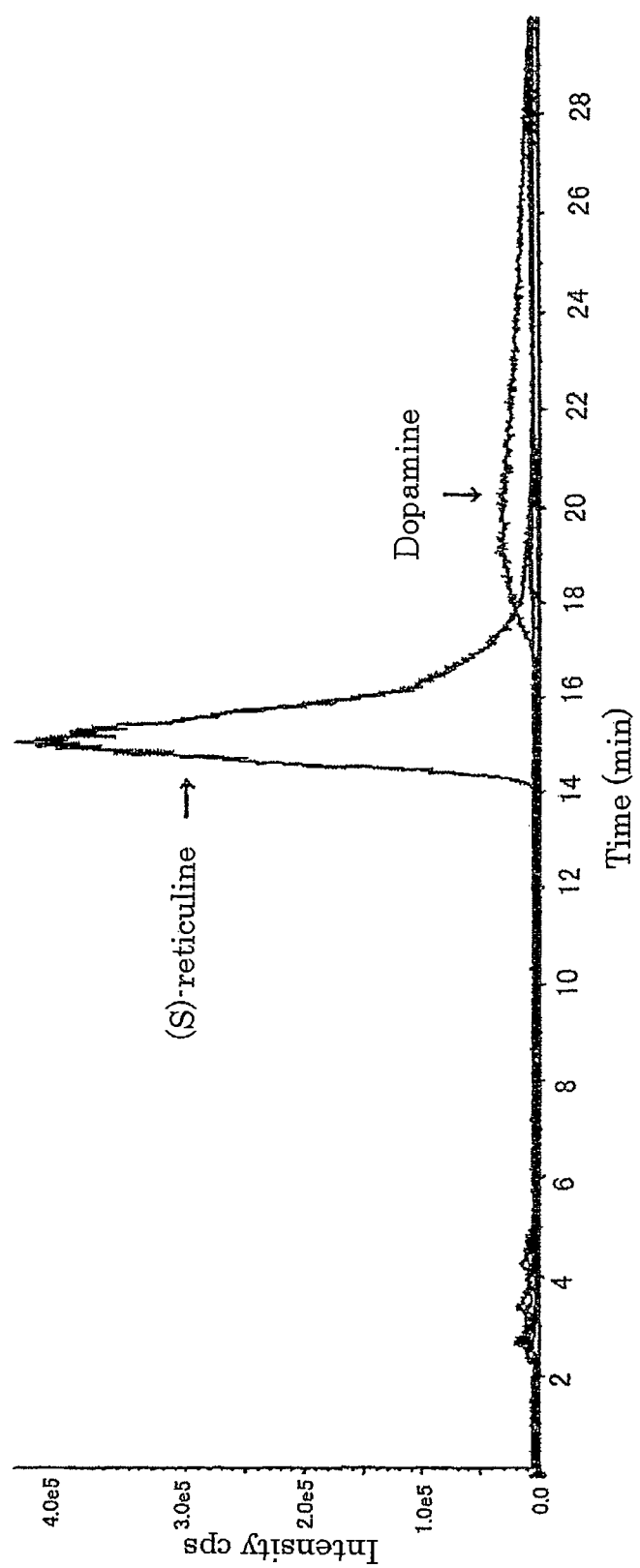
FIG. 4 shows LC-MS analysis of in vitro reticuline synthesis.

For optical resolution of reticuline, reticuline was eluted at a column temperature of 25° C. and a flow rate of 0.4 ml/min using a SUMICHIRAL-CBH column (Sumika Chemical Analysis Service, Ltd.). The mobile phase was 0.1% acetic acid-acetonitrile (95:5 [Vol/Vol], pH 7.0).
Results
In Vitro Reticuline Synthesis By using the enzyme extract, 22 mg/L of (S)-reticuline was synthesized from 2 mM dopamine. The reaction completely proceeded, and no intermediate product other than reticuline was observed (FIG. 4). By increasing a dopamine concentration up to 5 mM, the amount of synthesized (S)-reticuline was increased up to 55 mg/L.

The present inventors show first that a benzylisoquinoline alkaloid pathway was constructed in a microorganism system, and that *Escherichia coli* cells acquired the ability to produce a plant alkaloid. In the system of the present inventors, reticuline which is an intermediate product was successfully produced only from dopamine in *Escherichia coli*.

Example 4

Figure 5:
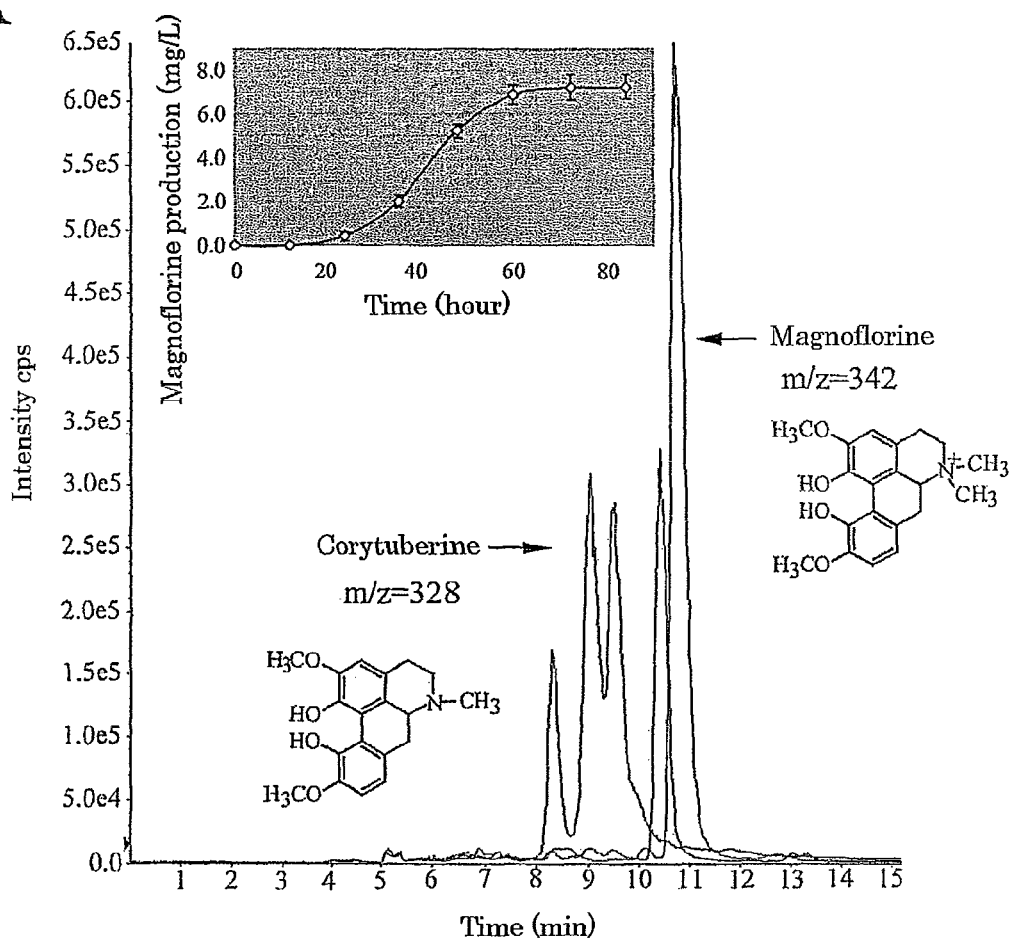
FIG. 5 shows products generated by combinations of enzymes, regarding synthesis of intermediate products from 3' hydroxynorcoclaurine to reticuline.

Biosynthesis of other intermediates in the benzylisoquinoline alkaloid pathway from 3'-hydroxynorcoclaurine (norlaudanosoline) to reticuline was investigated using transgenic *Escherichia coli* cells expressing biosynthesis genes (6OMT, CNMT and 4'OMT) of various combinations of methyltransferase enzymes. Results are shown in FIG. 5. As apparent from LC-MS analyses, it was shown that four types of benzylisoquinoline intermediates to (S)-reticuline were synthesized as main products using the in vitro method of the present inventors. Regarding the in vivo effective bioconversion, it was shown from the fact that medium becomes a bright color by a recombinant *Escherichia coli* cell with MAO, NCS and 6OMT introduced therein as compared to a recombinant *Escherichia coli* cell with no 6OMT introduced therein (the medium became black in the recombinant *Escherichia coli* with no 6OMT introduced therein). These results clearly show that CNMT or 4'OMT reaction does not proceed without 6OMT reaction which plays an important role in benzylisoquinoline alkaloid biosynthesis. These results are consistent with the facts that 6OMT is the rate limiting enzyme in *Coptis* cells, and that the activity of 4'OMT is controlled by N-methylation.

Example 5

Construction of Expression Vectors for Producing Magnoflorine/Scoulerine, and their Expressions in Budding Yeast A co-expression vector pGYR for P450 and yeast NADPH-P450 reductase was assigned from Dr. Y. Yabusaki, Sumitomo Chemicals Co., Ltd. This vector contained glyceroaldehyde-3-phosphate dehydrogenase promoter and terminator (Sakai T, Akiyoshi-Shibata M, Yabusaki Y, Ohkawa H (1992) Organella-targetted expression of rat liver cytochrome P450c27 in yeast. J Biol Chem 267: 16497-16502). The cloning site of pGYR was further modified to construct pGYR-SpeI so that SpeI site was contained. A full length CYP80G2 cDNA was amplified by PCR using a single-stranded cDNA synthesized using an oligo (dT) primer and SuperScript III RNase H-reverse transcriptase (Invitrogen) from 1.3 µg of total RNA of *Coptis* cultured cells, and ligated into SpeI site of pGYR-SpeI to construct an yeast expression vector, pGS-CYP80G2 (Ikezawa et al. Molecular cloning and characterization of CYP80G2, a cytochrome P450 which characterizes an intramolecular C—C phenol coupling of (S)-reticuline in magnoflorine biosynthesis, from cultured *Coptis japonica* cells. J Biol Chem) 283, 8810-8821, (2008)). An expression vector for CNMT was constructed as described below. A full length CNMT cDNA was amplified by PCR using KpnI-CNMT-F primer (5'-TATGGTACCATG-GCTGTGGAAGCAAAGCAA-3' (SEQ ID NO: 16)) and CNMT-SalI-R primer (5'-CCAGTCGACTCATTTTTTCT-TGAACAGAAC-3' (SEQ ID NO: 17)). The PCR product of CNMT gene was ligated into KpnI and SalI sites of pAUR123 vector (Takara Shuzo Co.) to construct an yeast expression vector, pAUR123-CNMT. For constructing an expressing vector for BBE, a full length BBE cDNA was amplified by PCR in the same manner as for GYP80G2, and ligated into HindIII and EcoRI sites of pYES2 vector (Invitrogen) to construct an yeast expression vector, pYES2-BBE (Ikezawa et al., unpublished data). As primers for making pYES2-BBE, HindIII-BBE-F primer (5'-ATAAAGCTTATTATGCGAG-CAACGCATACAATTATCTC-3' (SEQ ID NO: 18)) and BBE-YcoRI-R primer (5'-TGAATTCTTTAGATAA-CAATATTTCCTCTACATCCAACACC-3' (SEQ ID NO: 19)) were used.

For in vivo production of magnoflorine or scoulerine, expression plasmids for CYP80G2 and CNMT were introduced into an yeast strain AH22 (Oeda K, Sakaki T, Ohkawa H (1985) Expression of rat liver cytochrome P-450MC cDNA in *Saccharomyces cerevisiae*. DNA 4: 203-210) by LiCl method (Ito H, Fukuda Y, Murata K, Kimura A (1983) Transformation of intact yeast cells treated with alkali cations. J Bacteriol 153:163-168), and the expression plasmid for BBE was introduced into BJ5627. These recombinant yeast cells were cultured in SD medium at 28° C. and 180 rpm as described in the literature (Ikezawa N, et al. (2003) Molecular cloning and characterization of CYP719, a methylenedioxy bridge-forming enzyme that belongs to a novel P450 family, from cultured *Coptis japonica* cells. J Biol Chem 278: 38557-38565).

Production of Magnoflorine or Scoulerine in Microorganism

Figure 6:
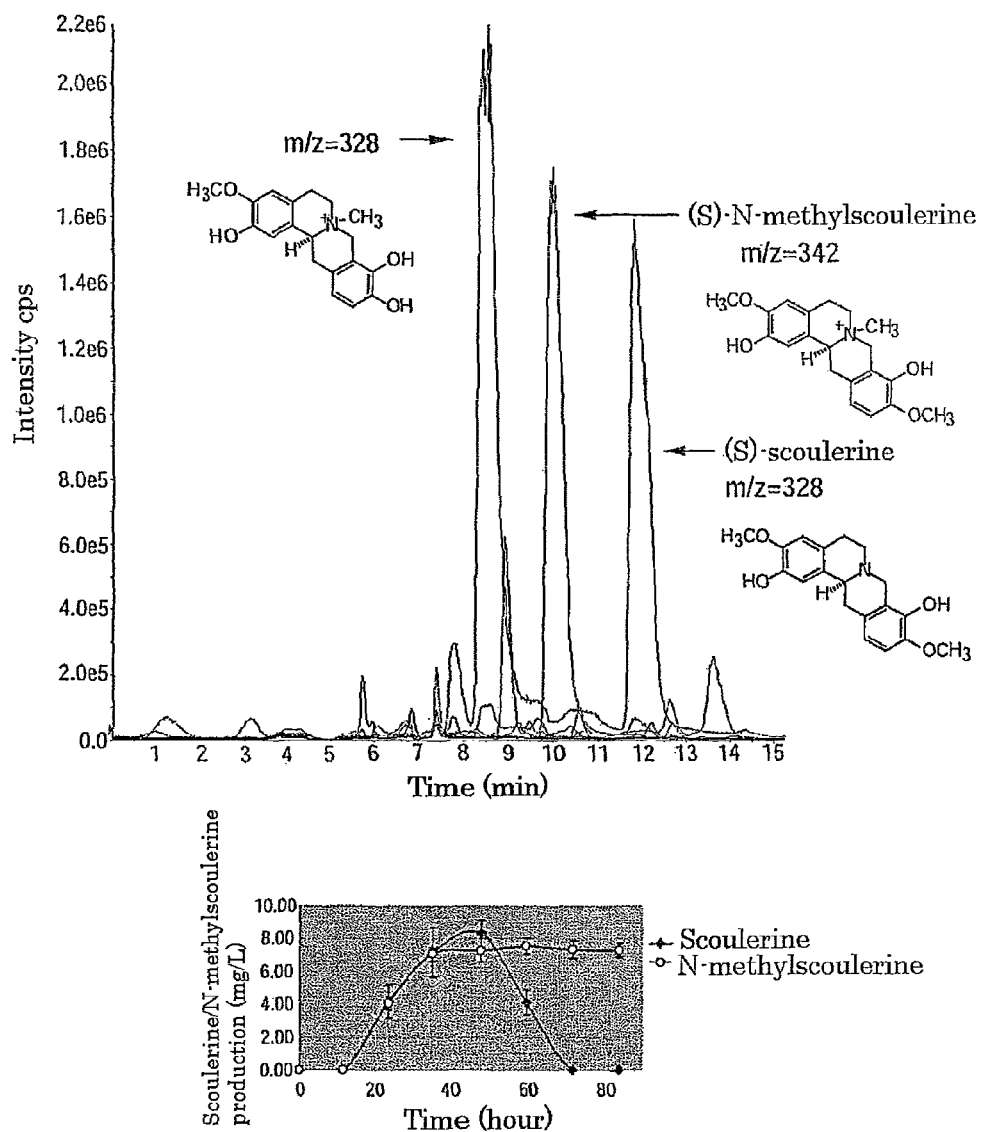
FIG. 6-A shows LC-MS analysis of magnoflorine produced by mixed culture of microorganisms.

For in vivo production of magnoflorine, the *Escherichia coli* cells were incubated with IPTG induction in LB medium containing 5 mM dopamine at 25° C. for 12 hours, and budding yeast cells expressing GYPG80G2 and CNMT were incubated in SD medium at 28° C. for 20 hours. Budding yeast cells and 2% glucose were added to the *Escherichia coli* medium, followed by further incubation at 28° C. for 72 hours. For scoulerine production, budding yeast cells expressing BBE and 2% galactose were added to the *Escherichia coli* medium, and incubation at 28° C. was further performed as in magnoflorine production for 48 hours. The media were recovered, and magnoflorine/scoulerine production was measured by LC-MS using the supernatants after precipitation of proteins with an equivalent volume of methanol (FIG. 6-A and FIG. 6-B).

LC-MS Analysis of Product

Production of benzylisoquinoline alkaloids was measured by LC-MS (API 3200™, Applied Biosystems Japan Ltd.) using Agilent™ HPLC system: column, ODS-80Ts (4.6×250 mm; Tosoh Inc.); solvent system, 20% acetonitrile containing 0.1% acetic acid; flow rate, 0.5 ml/min, 40° C. The product was identified by coelution with the standard chemical substance, and comparison with the standard chemical substance with respect to fragmentation spectrum in LS-MS/MS.

In order to distinguish reticuline in (R) and (S) forms, a chiral column (SUMICHIRAL CBH, 4.0×100 mm; Sumika Chemical Analysis Service) was used in LC-MS. Solvent system, 5% acetonitrile containing 0.1% acetic acid, having a pH of 7.0 adjusted with NH$_4$OH; flow rate, 0.4 ml/min, 25° C.

As the result of LC-MS, FIG. 6-A shows that magnoflorine (m/z 342) and corytuberine (m/z 328) were obtained. FIG. 6-B shows that (S)-scoulerine (m/z 328), and (S)—N-methylscoulerine (m/z 342) were obtained.

Example 6

Figure 7:
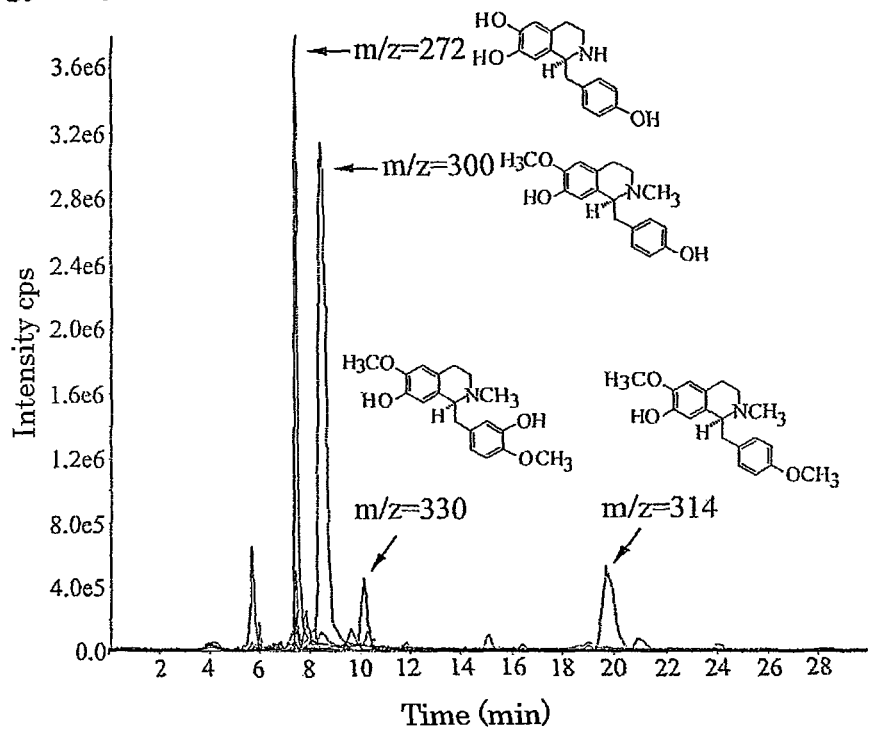
Figure 1:
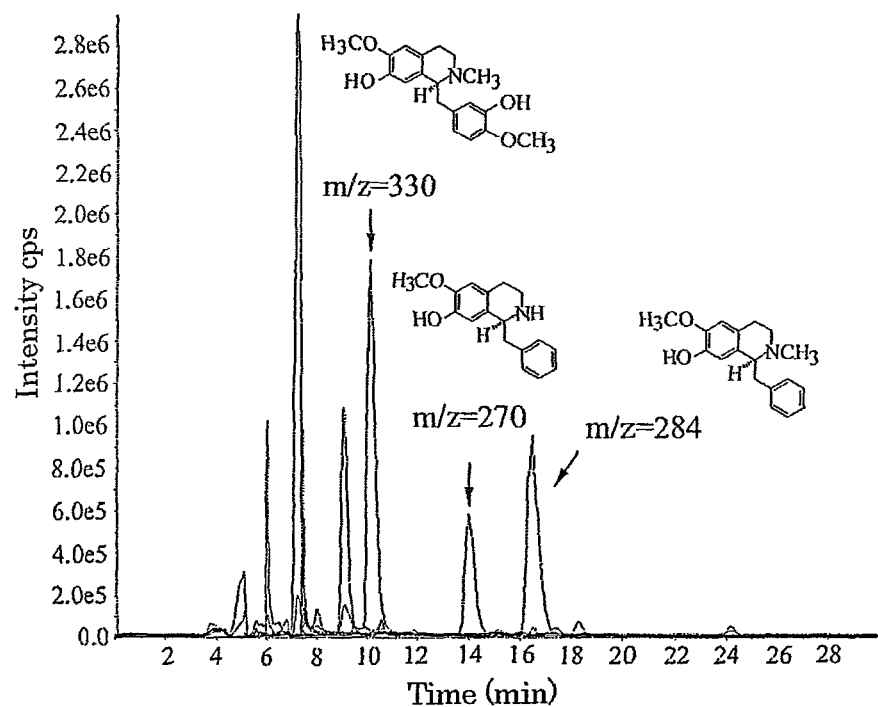
Figure 7:
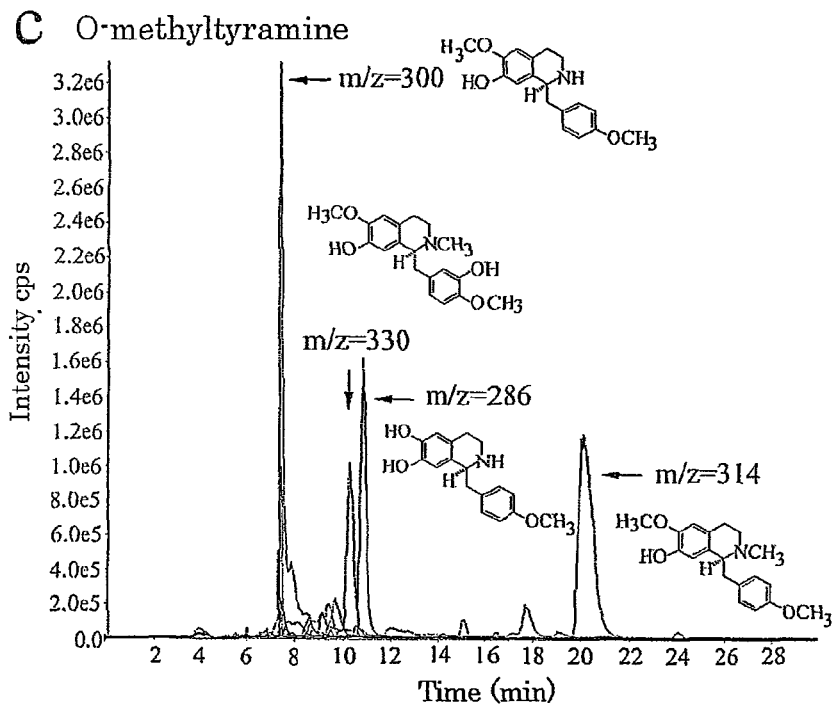
Figure 2:
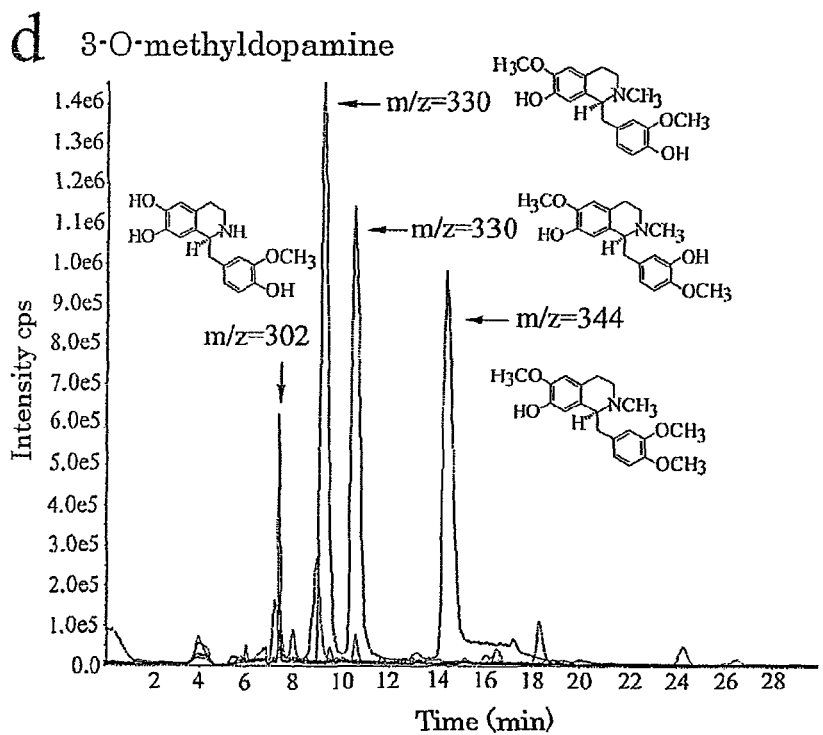
Figure 7:
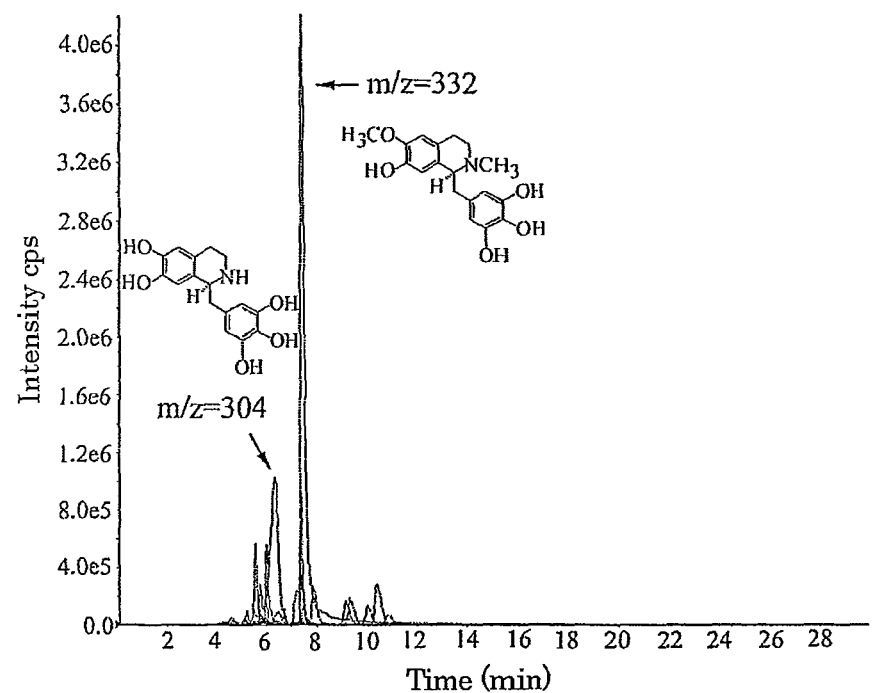
Figure 3:
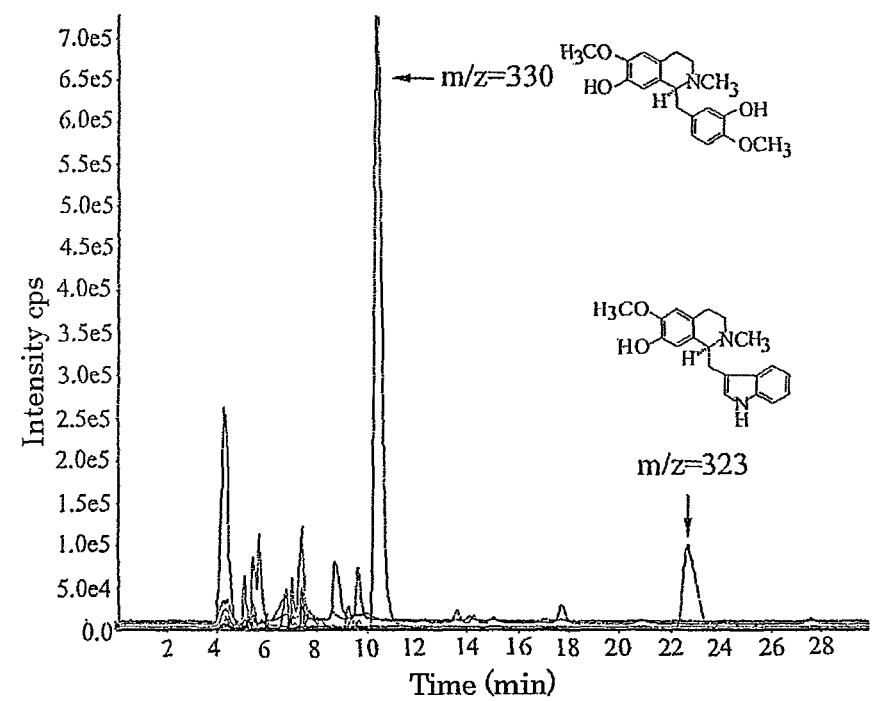

According to the same manner as that of Example 2, the *Escherichia coli* cells described in Example 1 were used to synthesize a variety of alkaloids in vivo. In this Example, as an amine to coexist with dopamine, tyramine, 2-phenylethylamine, O-methyltyramine, 3-O-methyldopamine, or 5-hydroxydopamine was used. In addition, according to the same manner as that of Example 3 except that tryptamine was present together with dopamine, synthesis of alkaloids in vitro was performed using the enzyme extract obtained from the *Escherichia coli* cells described in Example 1. Structures of, and results of LC-MS analyses of resulting alkaloids are shown in FIG. 7-1 to FIG. 7-3. From tyramine, 2-phenylethylamine, O-methyltyramine, 3-O-methyldopamine, 5-hydroxydopamine or tryptamine, in addition to reticuline, compounds which are thought to be norcoclaurine (m/z=272), N-methylcoclaurine (m/z=300), 4'-O-methyl-N-methylcoclaurine (m/z=314) (all above, copresence of tyramine), 7-isoquinolinol, 1,2,3,4-tetrahydro-6-methoxy-1-(phenylmethyl) (m/z=270), 7-isoquinolinol, 1,2,3,4-tetrahydro-6-methoxy-2-methyl-1-(phenylmethyl) (m/z=284) (all above, copresence of 2-phenylethylamine), 4'-O-methylnorcoclaurine (m/z=286), 4'-O-methyl-N-methylnorcoclaurine (m/z=300), 4'-O-methyl-N-methylcoclaurine (m/z=314) (all above, copresence of O-methyltyramine), 3'-O-methylnorcoclaurine (m/z=302), 3'-O-methyl-N-methylcoclaurine (m/z 330), 3'-O-methylreticuline (m/z=344) (all above, copresence of 3-O-methyldopamine), 3',5'-dihydroxynorcoclaurine (m/z=304), 3',5'-dihydroxy-4'-O-methylcoclaurine (m/z=332) (all above, copresence of 5-hydroxydopamine), or 6-O-methyl-7-hydroxy-indolylmethyl-1,2,3,4-tetrahydroisoquinoline (m/z=323) (copresence of tryptamine) were obtained, respectively.

INDUSTRIAL APPLICABILITY

Metabolic engineering which combines a microorganism enzyme gene and a plant-derived gene provides further advance of a microorganism system to pharmaceutical industry. According to the present invention, a new opportunity to produce an anti-malaria agent and an anti-cancer agent is developed, since initial steps in the benzylisoquinoline alkaloid biosynthesis from tyrosine to reticuline are common to biosynthesis of many isoquinoline alkaloids, and reticuline is a universal precursor of all benzylisoquinoline alkaloids.

The system of the present inventors enabled to produce a further intermediate having a novel or useful object. (S)-reticuline is converted into benzophenanthridine alkaloids, for example, sanguinarine and chelerythrine by BBE and P450-dependent oxidase, or is converted into aporphine alkaloids, for example, magnoflorine and isoboldine by CNMT and corytuberine synthase (CYP80G2; Ikezawa, N., Iwasa, K., and Sato, F., Molecular cloning and characterization of CYP80G2, a cytochrome P450 that catalyzes an intramolecular C—C phenol coupling of (S)-reticuline in magnoflorine biosynthesis, from cultured *Coptis japonica* cells. J. Biol. Chem. 283, 8810-8821 (2008)). This system can serve for fundament of a microorganism system for producing a wide range of benzylisoquinoline alkaloids.

The invention claimed is:

1. A method for producing reticuline from dopamine, which comprises the steps of:
providing a recombinant host cell expressing monoamine oxidase, norcoclaurine-6-O-methyltransferase, coclaurine-N-methyltransferase and 3'-hydroxy-N-methylcoclaurine-4'-O-methyltransferase, wherein the recombinant host cell is obtained by introducing genes encoding monoamine oxidase, norcoclaurine-6-O-methyltransferase, coclaurine-N-methyltransferase and 3'-hydroxy-N-methylcoclaurine-4'-O-methyltransferase into an isoquinoline alkaloid non-producing cell, and
culturing the recombinant host cell in the presence of dopamine,
wherein the recombinant host cell is an *Escherichia coli* cell, and wherein the origin of monoamine oxidase is from *Micrococcus luteus*, and the origin of norcoclaurine-6-O-methyltransferase, coclaurine-N-methyltransferase and 3'-hydroxv-N-methlcoclaurine-4'-O-methyltransferase are from *Coptis, and*
wherein the genes encoding monoamine oxidase consist of:
(a) a nucleotide sequence consisting of SEQ ID NO: 1; or
(b) a nucleotide sequence having 80% or more homology with the nucleotide sequence of SEQ ID NO: 1, and encoding a protein having monoamine oxidase activity,
wherein the genes encoding norcoclaurine-6-O-methyltransferase consist of:
(a) a nucleotide sequence consisting of SEQ ID NO: 3; or
(b) a nucleotide sequence having 80% or more homology with the nucleotide sequence of SEQ ID NO: 3, and encoding a protein having norcoclaurine-6-O-methyltransferase activity,
wherein the genes encoding coclaurine-N-methyltransferase consist of:
(a) a nucleotide sequence consisting of SEQ ID NO: 4; or
(b) a nucleotide sequence having 80% or more homology with the nucleotide sequence of SEQ ID NO: 4, and encoding a protein having coclaurine-N-methyltransferase activity,
wherein the genes encoding 3'-hydroxy-N-methylcoclaurine-4'-O-methyltransferase consist of:
(a) a nucleotide sequence consisting of SEQ ID NO: 5; or
(b) a nucleotide sequence having 80% or more homology with the nucleotide sequence of SEQ ID NO: 5, and encoding a protein having 3'-hydroxy-N-methylcoclaurine-4'-O-methyltransferase activity.

2. The method according to claim 1, wherein the recombinant host cell further expresses a gene encoding norcoclaurine synthase.

3. A method for producing reticuline from dopamine in vitro, which comprises the steps of:
providing a recombinant host cell expressing monoamine oxidase, norcoclaurine synthase, norcoclaurine-6-O-methyltransferase, coclaurine-N-methyltransferase and 3'-hydroxy-N-methylcoclaurine-4'-O-methyltransferase, wherein the recombinant host cell is obtained by introducing genes encoding monoamine oxidase, norcoclaurine synthase, norcoclaurine-6-O-methyltransferase, coclaurine-N-methyltransferase and 3'-hydroxy-N-methylcoclaurine-4'-O-methyltransferase, into an isoquinoline alkaloid non-producing cell,
obtaining an enzyme extract containing monoamine oxidase, norcoclaurine synthase, norcoclaurine-6-O-methyltransferase, coclaurine-N-methyltransferase and 3'-hydroxy-N-methylcoclaurine-4'-O-methyltransferase from the recombinant host cell,
providing a mixture of the enzyme extract and dopamine, and
producing the alkaloid from the mixture,
wherein the recombinant host cell is an *Escherichia coli* cell, and wherein the origin of monoamine oxidase is from *Micrococcus luteus*, and the origin of norcoclaurine-6-O-methyltransferase, coclaurine-N-methyltransferase and 3'-hydroxv-N-methlcoclaurine-4'-O-methyltransferase are from *Coptis, and*
wherein the genes encoding monoamine oxidase consist of:
(a) a nucleotide sequence consisting of SEQ ID NO: 1; or
(b) a nucleotide sequence having 80% or more homology with the nucleotide sequence of SEQ ID NO: 1, and encoding a protein having monoamine oxidase activity,
wherein the genes encoding norcoclaurine-6-O-methyltransferase consist of:
(a) a nucleotide sequence consisting of SEQ ID NO: 3; or
(b) a nucleotide sequence having 80% or more homology with the nucleotide sequence of SEQ ID NO: 3, and encoding a protein having norcoclaurine-6-O-methyltransferase activity,
wherein the genes encoding norcoclaurine synthase consist of:
(a) a nucleotide sequence consisting of SEQ ID NO: 2; or
(b) a nucleotide sequence having 80% or more homology with the nucleotide sequence of SEQ ID NO: 2, and encoding a protein having norcoclaurine synthase activity, wherein the genes encoding coclaurine-N-methyltransferase consist of:
(a) a nucleotide sequence consisting of SEQ ID NO: 4; or
(b) a nucleotide sequence having 80% or more homology with the nucleotide sequence of SEQ ID NO: 4, and encoding a protein having coclaurine-N-methyltransferase activity,
wherein the genes encoding 3'-hydroxy-N-methylcoclaurine-4'-O-methyltransferase consist of:
(a) a nucleotide sequence consisting of SEQ ID NO: 5; or
(b) a nucleotide sequence having 80% or more homology with the nucleotide sequence of SEQ ID NO: 5, and encoding a protein having 3'-hydroxy-N-methylcoclaurine-4'-O-methyltransferase activity.

4. The method according to claim 3, wherein reticuline is (S)-reticuline.

5. A method for producing an alkaloid from dopamine in vitro, which comprises the steps of:
providing a group of cells expressing monoamine oxidase, norcoclaurine synthase, norcoclaurine-6-O-methyltransferase, coclaurine-N-methyltransferase and 3'-hydroxy-N-methylcoclaurine-4'-O-methyltransferase,
wherein the group of cells consists of two or more types of cells each expressing one or more enzymes selected from the group consisting of monoamine oxidase, norcoclaurine synthase, norcoclaurine-6-O-methyltransferase, coclaurine-N-methyltransferase and 3'-hydroxy-N-methylcoclaurine-4'-O-methyltransferase, and contains at least one type of an isoquinoline alkaloid non-producing cell,
obtaining an enzyme extract containing monoamine oxidase, norcoclaurine synthase, norcoclaurine-6-O-methyltransferase, coclaurine-N-methyltransferase and 3'-hydroxy-N-methylcoclaurine-4'-O-methyltransferase from the group of cells,
providing a mixture of the enzyme extract and dopamine, and
producing the alkaloid from the mixture, wherein the group of cells are *Escherichia coli* cells, and wherein the origin of monoamine oxidase is from *Micrococcus luteus*, and the origin of norcoclaurine-6-O-methyltransferase, coclaurine-N-methyltransferase and 3'-hydroxy-N-methlcoclaurine-4'-O-methyltransferase are from *Coptis, and*
wherein the genes encoding monoamine oxidase consist of:
(a) a nucleotide sequence consisting of SEQ ID NO: 1; or
(b) a nucleotide sequence having 80% or more homology with the nucleotide sequence of SEQ ID NO: 1, and encoding a protein having monoamine oxidase activity,
wherein the genes encoding norcoclaurine-6-O-methyltransferase consist of:
(a) a nucleotide sequence consisting of SEQ ID NO: 3; or
(b) a nucleotide sequence having 80% or more homology with the nucleotide sequence of SEQ ID NO: 3, and encoding a protein having norcoclaurine-6-O-methyltransferase activity,
wherein the genes encoding norcoclaurine synthase consist of:
(a) a nucleotide sequence consisting of SEQ ID NO: 2; or
(b) a nucleotide sequence having 80% or more homology with the nucleotide sequence of SEQ ID NO: 2, and encoding a protein having norcoclaurine synthase activity, wherein the genes encoding coclaurine-N-methyltransferase consist of:
(a) a nucleotide sequence consisting of SEQ ID NO: 4; or
(b) a nucleotide sequence having 80% or more homology with the nucleotide sequence of SEQ ID NO: 4, and encoding a protein having coclaurine-N-methyltransferase activity,
wherein the genes encoding 3'-hydroxy-N-methylcoclaurine-4'-O-methyltransferase consist of:
(a) a nucleotide sequence consisting of SEQ ID NO: 5; or
(b) a nucleotide sequence having 80% or more homology with the nucleotide sequence of SEQ ID NO: 5, and encoding a protein having 3'-hydroxy-N-methylcoclaurine-4'-O-methyltransferase activity.

6. The method according to claim 5, wherein the alkaloid is (S)-reticuline.

7. The method according to claim 1, wherein the recombinant host cell is cultured in the presence of an amine other than dopamine in addition to dopamine.

8. The method according to claim 3, wherein the mixture of the enzyme extract and dopamine further comprises an amine other than dopamine.

9. The method according to claim 5, wherein the mixture of the enzyme extract and dopamine further comprises an amine other than dopamine.

10. The method according to claim 1, wherein monoamine oxidase consists of:
(a) a polypeptide sequence encoded by the nucleotide sequence of SEQ ID NO: 1, or
(b) a polypeptide sequence having 1 to 30 amino acids deleted, substituted or added in the polypeptide sequence encoded by the nucleotide sequence of SEQ ID NO: 1 having monoamine oxidase activity;
wherein norcoclaurine-6-O-methyltransferase consists of:
(a) a polypeptide sequence encoded by the nucleotide sequence of SEQ ID NO: 3, or
(b) a polypeptide sequence having 1 to 30 amino acids deleted, substituted or added in the polypeptide sequence encoded by the nucleotide sequence of SEQ ID NO: 3 having norcoclaurine 6-O-methyltransferase activity;
wherein coclaurine-N-methyltransferase consists of:
(a) a polypeptide sequence encoded by the nucleotide sequence of SEQ ID NO: 4, or
(b) a polypeptide sequence having 1 to 30 amino acids deleted, substituted or added in the polypeptide sequence encoded by the nucleotide sequence of SEQ ID NO: 4 having coclaurine-N-methyltransferase activity; and
wherein 3'-hydroxy-N-methylcoclaurine-4'-O-methyltransferase consists of:
(a) a polypeptide sequence encoded by the nucleotide sequence of SEQ ID NO: 5, or
(b) a polypeptide sequence having 1 to 30 amino acids deleted, substituted or added in the polypeptide sequence encoded by the nucleotide sequence of SEQ ID NO: 5 having 3'-hydroxy-N-methylcoclaurine-4'-O-methyltransferase activity.

11. The method according to claim 3, wherein monoamine oxidase consists of:
(a) a polypeptide sequence encoded by the nucleotide sequence of SEQ ID NO: 1, or
(b) a polypeptide sequence having 1 to 30 amino acids deleted, substituted or added in the polypeptide sequence encoded by the nucleotide sequence of SEQ ID NO: 1 having monoamine oxidase activity;

wherein norcoclaurine-6-O-methyltransferase consists of:
(a) a polypeptide sequence encoded by the nucleotide sequence of SEQ ID NO: 3, or
(b) a polypeptide sequence having 1 to 30 amino acids deleted, substituted or added in the polypeptide sequence encoded by the nucleotide sequence of SEQ ID NO: 3 having norcoclaurine 6-O-methyltransferase activity;

wherein coclaurine-N-methyltransferase consists of:
(a) a polypeptide sequence encoded by the nucleotide sequence of SEQ ID NO: 4, or
(b) a polypeptide sequence having 1 to 30 amino acids deleted, substituted or added in the polypeptide sequence encoded by the nucleotide sequence of SEQ ID NO: 4 having coclaurine-N-methyltransferase activity; and wherein 3'-hydroxy-N-methylcoclaurine-4'-O-methyltransferase consists of:
(a) a polypeptide sequence encoded by the nucleotide sequence of SEQ ID NO: 5, or
(b) a polypeptide sequence having 1 to 30 amino acids deleted, substituted or added in the polypeptide sequence encoded by the nucleotide sequence of SEQ ID NO: 5 having 3'-hydroxy-N-methylcoclaurine-4'-O-methyltransferase activity.

12. The method according to claim 5, wherein monoamine oxidase consists of:
(a) a polypeptide sequence encoded by the nucleotide sequence of SEQ ID NO: 1, or
(b) a polypeptide sequence having 1 to 30 amino acids deleted, substituted or added in the polypeptide sequence encoded by the nucleotide sequence of SEQ ID NO: 1 having monoamine oxidase activity;

wherein norcoclaurine-6-O-methyltransferase consists of:
(a) a polypeptide sequence encoded by the nucleotide sequence of SEQ ID NO: 3, or
(b) a polypeptide sequence having 1 to 30 amino acids deleted, substituted or added in the polypeptide sequence encoded by the nucleotide sequence of SEQ ID NO: 3 having norcoclaurine 6-O-methyltransferase activity;

wherein coclaurine-N-methyltransferase consists of:
(a) a polypeptide sequence encoded by the nucleotide sequence of SEQ ID NO: 4, or
(b) a polypeptide sequence having 1 to 30 amino acids deleted, substituted or added in the polypeptide sequence encoded by the nucleotide sequence of SEQ ID NO: 4 having coclaurine-N-methyltransferase activity; and wherein 3'-hydroxy-N-methylcoclaurine-4'-O-methyltransferase consists of:
(a) a polypeptide sequence encoded by the nucleotide sequence of SEQ ID NO: 5, or
(b) a polypeptide sequence having 1 to 30 amino acids deleted, substituted or added in the polypeptide sequence encoded by the nucleotide sequence of SEQ ID NO: 5 having 3'-hydroxy-N-methylcoclaurine-4'-O-methyltransferase activity.

13. The method according to claim 1, wherein the recombinant host cell further expresses a gene encoding norcoclaurine synthase and wherein the origin of norcoclaurine synthase is from *Coptis*.

14. The method according to claim 1, wherein the recombinant host cell further expresses a gene encoding norcoclaurine synthase and wherein the norcoclaurine synthase consists of:
(a) a polypeptide sequence encoded by the nucleotide sequence of SEQ ID NO: 2; or
(b) a polypeptide sequence having one or a few amino acids deleted, substituted or added in the polypeptide sequence encoded by a nucleotide sequence of SEQ ID NO: 2, and having enzymatic activity of NCS.

15. The method according to claim 1, wherein the recombinant host cell further expresses a gene encoding norcoclaurine synthase and wherein the gene encoding norcoclaurine synthase consists of:
(a) a nucleotide sequence consisting of SEQ ID NO: 2; or
(b) a nucleotide sequence having 80% or more homology with the nucleotide sequence of SEQ ID NO: 2, and encoding a protein having an enzyme activity of NCS.

* * * * *

SEQUENCE LISTING

<160> NUMBER OF SEQ ID NOS: 19

<210> SEQ ID NO 1
<211> LENGTH: 1332
<212> TYPE: DNA
<213> ORGANISM: Micrococcus luteus

<400> SEQUENCE: 1

```
atgagcaacc cgcatgtcgt gatcgtcgga gccggcttcg ccggcctggt ggccgcccgt      60
gaactgcaga tggcaggcgt ggacgtggag atcgtggagg cccgcgaccg cgtgggcggc     120
cgcgcctgga ccgaggagcg catgggccgt ccgctggaac tgggcgccac gtgggtgcac     180
tggatgcagc cgcacgtgtg gagcgagatc acccgctacg accagagcat ctacccccagc    240 ccgttctgcg acgacgccta ctggatcacc ggggccggg tggagcacgg caccgaggcg     300
gacctggatg ccgctctggc ccgccccatg gccaagatct tcgaggactc gcgggagttc     360
ttcccgtacc cgtacgagcc cctgcacgtg ctggacgaga gcagcggcag caccccggag    420
ctgcgggagc gcttccgcgc ggcggaccag ggcagtgtcc tggactgcct caagggcggc     480
gacttcaccc aggaggagcg ggacctgtgc gacgcgtact ggtccgccgc gtacatcggg     540
gacccgcacc aggggtcacc gctcatggcc aagcagtggg cggcgctgtc cgaccaccgg    600
ttgagcctgg tggacgagca gaccctgcgc ttcaagctca cccacggcat gcggggactg     660
tacgagaaca tcgccgcgga cctgcgctgc cccatccgcc tgaacacccc ggtcacggcg     720
gtcgaccacc gctccgacgg cgccacggtc accctgggca ccggcgagaa gatctcgtgc    780
gacagcgtga tcgtcacggt gccggtgggg gcgctgccaa ccatcgagtt cacccccgggc    840 ctgccctcgg ggatgcgcac cgtgatcgac cagcgctgga actccacggg ctgcaagatc    900
tgggtcaagg tcaagggcca ccacagcatc ctgggctacg ccccccacccc tcacaaggcc     960 gccgtgttcc gcagcgagtt cttcatggac gacgacacca ccatctgcgt gggcttcggc   1020
tcccaccacg acgccgtgga cctcaccgac ccgcgggacg cccaggcaat cgtggaccag   1080
tggcgccccg accttgaggt cgtggactgc acgggccacg actgggtggc ggacaggtgg   1140
agcggtcagg cgtgggccac gctgcgctca gggcagttca ccaacggctg gcaccacttc   1200
cgctccaccg actcgcggct gcgcttcgcc ggggcggact gggcgcgcgg ctggcgcggc   1260
gtggtggtgg acggcgccat cgagacgggc ctgtccaccg cccgggacgt cctccgggac   1320
atccgcgcct ga                                                       1332
```

<210> SEQ ID NO 2
<211> LENGTH: 591
<212> TYPE: DNA
<213> ORGANISM: Coptis japonica

<400> SEQUENCE: 2

| | | | | | |
|---|---|---|---|---|---|
| atgaggatgg | aagttgttct | agttgttttc | ttgatgttca | taggtacgat | aaattgtgaa | 60 |
| agattgatat | tcaatggacg | accgctactc | catcgcgtaa | caaaagagga | gactgtaatg | 120 |
| ctttatcatg | agctggaagt | agctgcttca | gccgatgaag | tgtggagtgt | cgaaggttcg | 180 |
| cctgagttgg | gcttgcattt | gcctgacttg | ctccctgctg | gtatatttgc | aaagtttgaa | 240 |
| attactggtg | atggaggtga | aggttcgatc | ctggacatga | cattcccccc | aggtcagttt | 300 |
| ccacatcatt | acagggagaa | gttcgtgttc | ttcgatcaca | gaatcgtta | caagttagta | 360 |
| gaacagatcg | atggtgattt | tttcgatcta | ggtgttacat | actatatgga | tacaatccga | 420 |
| gttgttgcga | caggccctga | ttcatgtgtc | atcaagtcta | ctactgaata | ccatgtgaaa | 480 |
| cctgagtttg | ccaaaatcgt | caaaccactt | attgacactg | ttccactagc | tatcatgtct | 540 |
| gaagcgattg | caaaggttgt | tctagagaac | aaacacaaga | gttcagagta | a | 591 |

<210> SEQ ID NO 3
<211> LENGTH: 1044
<212> TYPE: DNA
<213> ORGANISM: Coptis japonica

<400> SEQUENCE: 3

| | | | | | |
|---|---|---|---|---|---|
| atggaagtga | agaaggacaa | tctctcatct | caagctaaac | tgtggaactt | catttatggt | 60 |
| tttgctgaat | cactagtcct | caaatgtgca | gtgcaacttg | atctagccaa | cataattcac | 120 |
| aacagtggca | cgtccatgac | tctttccgag | ttatcttcgc | gtcttccaag | tcaacctgtc | 180 |
| aatgaagacg | ccttgtatcg | agtcatgcgt | tacttggttc | acatgaagct | attcacaaaa | 240 |
| gcatcaatag | atggagaact | aagatatgga | cttgcaccac | cagctaagta | tcttgttaaa | 300 |
| ggttgggata | aatgtatggt | tggctcaatt | ttagcaatca | ctgataaaga | tttcatggca | 360 |
| ccatggcatt | accttaagga | tggattatca | ggcgaaagtg | gtacagcgtt | tgagaaggcc | 420 |
| ttggggacga | atatatgggg | gtacatggca | gagcaccctg | agaaaaacca | gctatttaat | 480 |
| gaagcaatgg | ctaatgattc | aaggcttatt | atgtctgcat | tggtgaaaga | atgtggaaat | 540 |
| atttttaatg | gtataactac | acttgtggat | gttggtggtg | gtactggaac | tgctgtgagg | 600 |
| aatattgcca | atgcatttcc | acatataaag | tgtactgttt | atgatcttcc | tcatgtcatt | 660 |
| gctgattctc | ctgggtactc | cgaagttcat | tgcgtggcag | gtgatatgtt | caagttcata | 720 |
| ccaaaggctg | atgctatcat | gatgaagtgc | atccttcacg | actgggatga | caaagaatgc | 780 |
| attgaaattc | taaagcgatg | caaggaggca | gtaccagtca | aaggcgggaa | agtgattata | 840 |
| gtcgacattg | tcttaaatgt | gcaatcagaa | catccttata | ccaagatgag | actgactttg | 900 |
| gatttggaca | tgatgctcaa | cactggagga | aaagagagga | ctgaagagga | atggaagaag | 960 |
| ctcatccatg | atgcagggta | caagggcat | aagataacac | aaattactgc | tgtacaatct | 1020 |
| gtgattgagg | cttatccata | ttag | | | | 1044 |

<210> SEQ ID NO 4
<211> LENGTH: 1077
<212> TYPE: DNA
<213> ORGANISM: Coptis japonica

```
<400> SEQUENCE: 4
atggctgtgg aagcaaagca aacaaagaag gcagccatag tagagttgtt aaaacagttg      60
gagctgggct tggttccata tgatgatatt aagcagctca taaggaggga actggcaagg     120
cgcctgcaat ggggttataa acctacttat gaagaacaaa tagctgaaat ccaaaactta     180
actcattctc tgcgacaaat gaaaattgca acagaggttg agaccttgga ttcacaattg     240
tacgagattc ctattgagtt tctaaagatt atgaatggaa gtaacttaaa aggaagttgt     300
tgctacttca agaagattc aacaacatta gatgaagctg agatagcgat gctggattta     360
tactgcgaga gagctcaaat ccaagatgga cagagtgttc ttgatcttgg atgtgggcaa     420
ggagctctta cattacatgt tgcacagaaa tataaaaact gtcgcgtaac agcagtaaca     480
aattcagttt cacaaaaaga gtacattgaa gaagaatcaa ggagacgtaa tttgttgaat     540
gtggaagtca aattggcaga cataaccaca catgagatgg ctgagacata cgatcgtatt     600
ttggtaatag agttgtttga gcacatgaag aactatgaac ttctcctgag gaaaatctca     660
gagtggatat cgaaagatgg gcttctcttt ctagagcaca tatgccacaa gacctttgct     720
taccactatg agcctctaga cgacgacgat tggtttacag agtacgtgtt tcctgctggg     780
actatgatca taccatctgc atcgttcttt ttgtatttcc aggatgacgt ttcggttgtg     840
aaccattgga ctcttagtgg gaagcacttt tcgcgtacca tgaggaatg gttgaagaga     900 ttggacgcaa accttgatgt tattaaacca atgtttgaga ctttaatggg aaatgaggaa     960
gaggcagtga agttgattaa ctattggaga ggattttgtt tatctggaat ggaaatgttt    1020
ggatataaca atggtgaaga atggatggca agtcatgttc tgttcaagaa aaaatga      1077

<210> SEQ ID NO 5
<211> LENGTH: 1053
<212> TYPE: DNA
<213> ORGANISM: Coptis japonica

<400> SEQUENCE: 5
atggctttcc atgggaaaga tgatgttctg gacatcaaag ctcaagctca tgtgtggaaa      60
atcatctatg gttttgcaga ttccctagtc ctccgatgtg cagtggaact tggaatcgtc     120
gacatcattg ataacaacaa ccaacccatg gcacttgccg atctggcatc taagcttcct     180
gtttccgatg tgaattgcga taatttgtat cggatattac gatacttggt gaaaatggaa     240
atactgagag tggaaaaatc tgatgatggt cagaagaagt acgcgcttga acctattgca     300
acattgcttt caaggaatgc gaagaggagt atggttccaa tgattcttgg aatgactcaa     360
aaagatttta tgactccttg gcattcaatg aaggatggct taagtgacaa tggtactgct     420
tttgagaagg ccatgggaat gactatatgg gagtacttgg aaggacaccc tgatcaaagc     480
caattattca tgaaggcat ggccggtgaa acaaggcttc tcacttcttc actcatatct     540
ggaagtagag atatgtttca aggtattgac tcacttgttg atgttggtgg aggaaatggt     600
actactgtca aggccatttc tgacgcattt ccacatatca agtgcacccct ctttgatctc     660 cctcatgtca ttgccaattc ctatgacctt cctaatattg aacgaattgg tggcgacatg     720
tttaaatccg tgcccagtgc ccaagctatc atactcaagc taattttgca cgattggaat     780
gacgaagact cgatcaagat tttaaagcaa tgcagaaatg cagtgccaaa agatggagga     840
aaagtgatta gtggatgt ggcattagat gaggagtcag accatgagct tagcagcaca     900
cgattgatcc ttgatatcga tatgttggtg aacactggtg gtaaagagcg gactaaagag     960
```

-continued

```
gtttgggaga aaattgtgaa aagtgcagga tttagtggtt gcaaaatcag gcacatagcg      1020
gctatacaat cagtcattga ggtttttcca tag                                   1053
```

<210> SEQ ID NO 6
<211> LENGTH: 29
<212> TYPE: DNA
<213> ORGANISM: Artificial
<220> FEATURE:
<223> OTHER INFORMATION: PCR primer

<400> SEQUENCE: 6

```
ttgaattcat gagcaacccg catgtcgtg                                          29
```

<210> SEQ ID NO 7
<211> LENGTH: 28
<212> TYPE: DNA
<213> ORGANISM: Artificial
<220> FEATURE:
<223> OTHER INFORMATION: PCR primer

<400> SEQUENCE: 7

```
ctaagcttca ggcgcggatg tcccggag                                           28
```

<210> SEQ ID NO 8
<211> LENGTH: 26
<212> TYPE: DNA
<213> ORGANISM: Artificial
<220> FEATURE:
<223> OTHER INFORMATION: PCR primer

<400> SEQUENCE: 8

```
actcgcgatc ccgcgaaatt aatacg                                             26
```

<210> SEQ ID NO 9
<211> LENGTH: 28
<212> TYPE: DNA
<213> ORGANISM: Artificial
<220> FEATURE:
<223> OTHER INFORMATION: PCR primer

<400> SEQUENCE: 9

```
caggatccag caaaaaaccc ctcaagac                                           28
```

<210> SEQ ID NO 10
<211> LENGTH: 27
<212> TYPE: DNA
<213> ORGANISM: Artificial
<220> FEATURE:
<223> OTHER INFORMATION: PCR primer

<400> SEQUENCE: 10

```
aggtaccgat cccgcgaaat taatacg                                            27
```

<210> SEQ ID NO 11
<211> LENGTH: 29
<212> TYPE: DNA
<213> ORGANISM: Artificial
<220> FEATURE:
<223> OTHER INFORMATION: PCR primer

<400> SEQUENCE: 11

```
cagatctaat atggataagc ctcaatcac                                          29
```

```
<210> SEQ ID NO 12
<211> LENGTH: 27
<212> TYPE: DNA
<213> ORGANISM: Artificial
<220> FEATURE:
<223> OTHER INFORMATION: PCR primer

<400> SEQUENCE: 12
cagatctgat cccgcgaaat taatacg                              27

<210> SEQ ID NO 13
<211> LENGTH: 29
<212> TYPE: DNA
<213> ORGANISM: Artificial
<220> FEATURE:
<223> OTHER INFORMATION: PCR primer

<400> SEQUENCE: 13
tggatcctat ggaaaaacct caatgactg                            29

<210> SEQ ID NO 14
<211> LENGTH: 27
<212> TYPE: DNA
<213> ORGANISM: Artificial
<220> FEATURE:
<223> OTHER INFORMATION: PCR primer

<400> SEQUENCE: 14
tggatccgat cccgcgaaat taatacg                              27

<210> SEQ ID NO 15
<211> LENGTH: 30
<212> TYPE: DNA
<213> ORGANISM: Artificial
<220> FEATURE:
<223> OTHER INFORMATION: PCR primer

<400> SEQUENCE: 15
acctgcaggc agcaaaaaac ccctcaagac                           30

<210> SEQ ID NO 16
<211> LENGTH: 30
<212> TYPE: DNA
<213> ORGANISM: Artificial
<220> FEATURE:
<223> OTHER INFORMATION: PCR primer

<400> SEQUENCE: 16
tatggtacca tggctgtgga agcaaagcaa                           30

<210> SEQ ID NO 17
<211> LENGTH: 30
<212> TYPE: DNA
<213> ORGANISM: Artificial
<220> FEATURE:
<223> OTHER INFORMATION: PCR primer

<400> SEQUENCE: 17
ccagtcgact cattttttct tgaacagaac                           30

<210> SEQ ID NO 18
<211> LENGTH: 38
<212> TYPE: DNA
<213> ORGANISM: Artificial
<220> FEATURE:
<223> OTHER INFORMATION: PCR primer
```

```
<400> SEQUENCE: 18
ataaagctta ttatgcgagc aacgcataca attatctc                            38

<210> SEQ ID NO 19
<211> LENGTH: 41
<212> TYPE: DNA
<213> ORGANISM: Artificial
<220> FEATURE:
<223> OTHER INFORMATION: PCR primer

<400> SEQUENCE: 19
tgaattcttt agataacaat atttcctcta catccaacac c                        41
```